US009169465B2

(12) United States Patent
Zuckermann

(10) Patent No.: US 9,169,465 B2
(45) Date of Patent: *Oct. 27, 2015

(54) NON-SIMIAN CELLS FOR GROWTH OF PORCINE REPRODUCTIVE AND RESPIRATORY SYNDROME (PRRS) VIRUS

(71) Applicant: The Board of Trustees of the University of Illinois, Urbana (IL)

(72) Inventor: Federico A. Zuckermann, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/181,460

(22) Filed: Feb. 14, 2014

(65) Prior Publication Data

US 2014/0162362 A1 Jun. 12, 2014

Related U.S. Application Data

(60) Continuation of application No. 13/475,444, filed on May 18, 2012, now Pat. No. 8,663,984, which is a division of application No. 12/013,236, filed on Jan. 11, 2008, now Pat. No. 8,202,717.

(60) Provisional application No. 60/884,782, filed on Jan. 12, 2007, provisional application No. 60/956,597, filed on Aug. 17, 2007.

(51) Int. Cl.
*C12N 5/071* (2010.01)
*C12N 7/00* (2006.01)

(52) U.S. Cl.
CPC ................ *C12N 5/0688* (2013.01); *C12N 7/00* (2013.01); *C12N 2501/22* (2013.01); *C12N 2770/10051* (2013.01)

(58) Field of Classification Search
None
See application file for complete search history.

(56) References Cited

U.S. PATENT DOCUMENTS

| | | | |
|---|---|---|---|
| 5,476,778 | A | 12/1995 | Chladek et al. |
| 5,510,258 | A | 4/1996 | Sanderson et al. |
| 5,583,053 | A | 12/1996 | Kim |
| 5,587,164 | A | 12/1996 | Sanderson et al. |
| 5,698,203 | A | 12/1997 | Visser et al. |
| 5,840,563 | A | 11/1998 | Chladek et al. |
| 5,846,805 | A | 12/1998 | Collins et al. |
| 5,925,359 | A | 7/1999 | Van Woensel et al. |
| 5,989,563 | A | 11/1999 | Chladek et al. |
| 6,033,844 | A | 3/2000 | Visser et al. |
| 6,042,830 | A | 3/2000 | Chladek et al. |
| 6,110,468 | A | 8/2000 | Collins et al. |
| 6,197,310 | B1 | 3/2001 | Wensvoort et al. |
| 6,210,963 | B1 | 4/2001 | Haddada et al. |
| 6,241,990 | B1 | 6/2001 | Collins et al. |
| 6,251,404 | B1 | 6/2001 | Paul et al. |
| 6,455,245 | B1 | 9/2002 | Wensvoort et al. |
| 6,498,008 | B2 | 12/2002 | Collins et al. |
| 6,500,662 | B1 | 12/2002 | Calvert et al. |
| 6,660,513 | B2 | 12/2003 | Mengeling et al. |
| 6,806,086 | B2 | 10/2004 | Wensvoort et al. |
| 7,081,342 | B2 | 7/2006 | Mengeling et al. |
| 7,388,087 | B2 | 6/2008 | Zuckermann et al. |
| 8,202,717 | B2 | 6/2012 | Zuckermann |
| 8,663,984 | B2 | 3/2014 | Zuckermann |
| 2003/0219460 | A1 | 11/2003 | David et al. |
| 2005/0271685 | A1 | 12/2005 | Calvert et al. |
| 2006/0063151 | A1 | 3/2006 | Roof et al. |
| 2012/0231540 | A1 | 9/2012 | Zuckermann |

FOREIGN PATENT DOCUMENTS

| | | | | |
|---|---|---|---|---|
| EP | 0610250 | | 8/1994 | |
| WO | WO 93/07898 | | 4/1993 | |
| WO | WO 98/35023 | * | 8/1998 | .............. C12N 7/00 |
| WO | WO 98/55626 | | 12/1998 | |
| WO | WO 2005/107796 A2 | | 11/2005 | |
| WO | WO 2008/089094 A2 | | 7/2008 | |

OTHER PUBLICATIONS

Thanawongnuwech et al (Veterinary Microbiology 63:177-187, 1998).*
Winkler et al (Journal of Leukocyte Biology 38:471-480, 1985).*
Rowland et al (Veterinary Microbiology 96:219-235 (2003).*
Lehman-Grube (Arch Gesamte Virusforsch. 14:1-14, 1963).*
Morton (Journal of Luekocyte Biology 43:403-410, 1988).*
American Type Culture Collection (ATCC), Product Description describing CRL-11171 (obtained as accessed from ATCC website, Nov. 21, 2011).
Bautista et al. (Apr. 1993) "Comparison of Porcine Alveolar Macrophages and CL2621 for the Detection of Porcine Reproductive and Respiratory Syndrome (PRRS_ Virus and Anti-PRRS Antibody," *J. Vet. Diagn. Invest*. 5(2):163-165.
Bridell et al. (Jun. 15, 1992) "Further Phenotypic Characterization and Isolation of Human Hematopoietic Progenitor Cells Using a Monoclonal Antibody to the *c-kit* Receptor," *Blood* 79(12):3159-3167.
Carillo et al. (2006) "Isolation and Characterization of Immortalized Porcine Aortic Endothelial Cell Lines," *Vet. Immunol. Immunopathol*. 89:91-98.
Choi et al. (2006), "Identification of 5' and 3' cis-Acting Elements of the Porcine Reproductive and Respiratory Syndrome Virus: Acquisition of Novel 5' AU-Rich Sequences Restored Replication of a 5'-Proximal 7-Nucleotide Deletion Mutant," Journal of Virology 80:723-736.
Chiou et al. (2000) "Effects of Porcine Reproductive and Respiratory Syndrome Virus (isolate tw91) on Porcine Alveolar Macrophages in Vitro," *Veterinary Microbiology* 71(1-2):9-25.
Counter et al. (1998) "Telomerase Activity is Restored in Human Cells by Ectopic Expression of hTERT (hEST2), the Catalytic Subunit of Telomerase," *Oncogene* 16:1217-1222.

(Continued)

*Primary Examiner* — Mary E Mosher
(74) *Attorney, Agent, or Firm* — Lathrop & Gage LLP

(57) ABSTRACT

Disclosed are compositions and methods relating to growth of Porcine Reproductive and Respiratory Syndrome Virus (PRRSV) using non-simian cells. In a particular example, porcine alveolar macrophage cells are described as having a capability of supporting infectivity and reproduction by PRRSV. Cells and cell lines of the invention are disclosed in connection with applications relating to PRRS disease, including vaccine technologies.

20 Claims, 9 Drawing Sheets

(56) References Cited

OTHER PUBLICATIONS

Delputte et al. (Aug. 2004) "Porcine Arterivirus Infection of Alveolar Macrophages is Mediated by Sialic Acid on the Virus," *J. Virol.* 78(15):8094-8101.

Delputte et al. (May 2002) "Involvement of the Matrix Protein in Attachment of Porcine Reproductive and Respiratory Syndrome Virus to a Heparinlike Receptor on Porcine Alveolar Macrophages," *J. Virol.* 76(9):4312-4320.

Delputte et al. (2007), "IFN-α Treatment Enhances Porcine Arterivirus Infection of Monocytes via Upregulation of the Porcine Arterivirus Receptor Sialoadhesin," Journal of Interferon & Cytokine Research 27: 757-766.

Delrue et al. (2010), "Susceptible cell lines for the production of porcine reproductive and respiratory syndrome virus by stable transfection of sialoadhesin and CD163," BMC Biotechnology 10:48, p. 1-12.

Duan et al., Effects of original and state of differentiation and activation of monocytes/macrophages on their susceptibility to porcine reproductive and respiratory syndrome virus (PRRSV), Archives of Virology 142:2483-2497, 1997.

Gallo, R.C. (2002) "Historical Essay. The Early Years of HIV/AIDS," *Science* 298(5599):1728-1730.

Harms et al. (2001) "Experimental Reproduction of Severe Disease in CD/CD Pigs Concurrently Infected with Type 2 Porcine Circovirus and Porcine Reproductive and Respiratory Syndrome Virus," *Vet. Pathol.* 38:528-539.

Helmke et al. (Aug. 1987) "From Growth Factor Dependence to Growth Factor Responsiveness: The Genesis of an Alveolar Macrophage Cell Line," *In. Vitro Cell. Dev. Biol.* 23(8):567-574.

Herscowitz et al., Maintenance of macrophages in vitro, Chapter 21, in: Manual of Macrophage Methodology, Herscowitz et al. editors, Marcel Dekker, Inc., New York, 1981, pp. 161-165.

Hill et al. (2004) "PRRS Control: To Hell and Back," American Association of Swine Veterinarians, Des Moines, Iowa, USA, Mar. 6-9, pp. 369-376 (Article Summary).

International Search Report, Corresponding to International Application No. PCT/US08/50908, Mailed Sep. 12, 2008.

Johnson et al. (2004) "Pathogenic and Humoral Immune Response to Porcine Reproductive and Respiratory Virus (PRRSV) are Related to Viral Load in Acute Infection," *Vet. Immunol. Immunopathol.* 102:233-247.

Kim et al. (Aug. 2005) "Establishment and Characterization of Endothelial Cell Lines from the Aorta if Miniature Pig for the Study of Xenotransplantation," *Cell Biol. Int.* 29(8):638-646.

Kwak et al. (2006) "Establishment of Immortal Swine Kidney Epithelial Cells," *Animal Biotechnol.* 17:51-58.

Kwon et al. (Nov. 30, 2006) "Infectious Clone-Derived Viruses from Virulent and Vaccine Strains of Porcine Reproductive and Respiratory Syndrome Virus Mimic Biological Properties of Their Parental Viruses in a Pregnant Sow Model," *Vaccine* 24(49-50):7071-7180.

Lager et al., Gross and microscopic lesions in porcine fetuses infected with porcine reproductive and respiratory syndrome virus, J Jet Diagn Invest 8:275-282, Jul. 1, 1996.

Lowe et al. (2005) "Correlation of Cell-Mediated Immunity Against Porcine Reproductive and Respiratory Syndrome Virus with Protection Against Reproductive Failure in Sows During Outbreaks of Porcine Reproductive and Respiratory Syndrome in Commercial Herds," *J. Am. Vet. Med. Assoc.* 226:1707-1711.

Mayani et al. (May 1, 1994) "Thy-1 Expression Is Lined to Functional Properties of Primitive Hematopoietic Progenitor Cells from Human Umbilical Cord Blood," *Blood* 83(9):2410-2417.

McAteer et al., Basic cell culture technique and the maintenance of cell lines, Chapter 4, in: Basic Cell Culture, Davis editor, Oxford University Press, New York, 1994, pp. 93-98.

Meier et al. (2000) "Characteristics of the Immune Response of Swine to PRRS Virus," *Vet. Res.* 31:41.

Meier et al. (2003) "Gradual Development of the Interferon-g Response of Swine to Porcine Reproductive and Respiratory Syndrome Virus," *Virol.* 309:18-31.

Meier et al. (2004) "Cytokines and Synthetic Double-Stranded RNA Augment the T Helper Immune Response of Swine to Porciens Reproductive and Resiratory Syndrome Virus," *Vet. Immunol. Immunopathol.* 102:299-314.

Meng et al. (1996) "Characterization of a High-Virulence US Isolate of Porcine Reproductive and Respiratory Syndrome Virus in a Continuous Cell Line, ATCC CRL11171," *J. Vet. Deagn. Invest.* 8:374-381.

Mengeling et al. (1996) "Comparison Among Strains of Porcine Reproductive and Respiratory Syndrome Virus for Their Ability to Cause Reproductive Failure," *Am. J. Vet. Res.* 57:834-839.

Mengeling et al. (1999) "Safety and Efficacy of Vaccination of Pregnant Gilts Against Porcine Reproductive and Respiratory Syndrome," *Am. J. Vet. Res.* 60:796-801.

Mengeling et al., Diagnosis of porcine reproductive and respiratory syndrome, J Vet Diagn Invest 7:3-16, 1995.

Naviaux et al. (Aug. 1996) "The pCL Vector System: Rapid Production of Helper-Free, High-Titer, Recombinant Retroviruses," *J. Virol.* 70(8):5701-5705.

Neumann et al. (Aug. 1, 2005) "Assessment of the Economic Impact of Porcine Reproductive and Respiratory Syndrome on Swine Production in the United States," *J. Am. Vet Med. Assoc.* 227(3):385-392.

OIE Terrestrial Manual, Porcine reproductive and respiratory syndrome, Chaper 2.8.7, May 2010, pp. 1-13.

Opriessnig et al. (Dec. 2002) "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV," *J. Virol.* 76(23):11837-11844.

Osorio et al. (1998) "PRRSV: Comparison of Commercial Vaccines in Their Ability to Induce Protection Against Current PRRSV Strains of Higher Virulence," *Allen D. Leman Swine Conference* 25:176-182.

Rossow et al., Experimental porcine reproductive and respiratory syndrome virus infection in one-, four-, and 10-week-old pigs, J Vet Diagn Invest 6:3-12, Jan. 1, 1994.

Sanchex-Torres et al. (2003) "Expression of Porcine CD163 on Monocytes/Machrophages Correlates with Permissiveness to African Wine Fever Infection," *Arch. Virol.* 148:2307-2323.

Sanchez et al. (1999) "The Porcine 2A10 Antigen is Homologous to Human CD163 and Related to Macrophage Differentiation," *J. Immunol.* 162:5230-5237.

Schmeisser et al. (Feb. 16, 2001) "Monocytes Coexpress Endothelial and Macrophagocytic Lineage Markers and Form Cord-Like Structures in Matrigel Under Angiogenic Conditions," *Cardiovasc. Res.* 49(3):671-680.

Schnitzlein et al. (1998) "Determination of the Specificity of CD45 and CD45R Monoclonal Antibodies Through the Use of Transfected Hamster Cells Producing Individual Porcine CD45 Isoforms," *Vet. Immunol. Immunopathol.* 60:389-401.

Shanmukhappa et al. (Jun. 16, 2007) "Role of CD151, A Tetraspanin, in Porcine Reproductive and Respiratory Syndrome Virus Infection," *Virology* 4:62.

Supplementary European Search Report, Application No. EP08727607, Oct. 12, 2010, 8 pages.

Thanawongnuwech R. et al., The role of pulmonary intravascular macrophases in porcine reproductive and respiratory syndrome virus infection, Animal Health Research Reviews 1(2):95-102, 2000.

Thanawongnuwech R., et al., Vet Microbiol. Oct. 1998;63(2-4):177-87, Influence of pig age on virus titer and bactericidal activity of porcine reproductive and respiratory syndrome virus (PRRSV)-infected pulmonary intravascular macrophages (PIMs).

Van den Heuvel M. M. et al., Regulation of CD163 on human macrophages; cross-linking of CD163 induces signaling and activation, Journal of Leukocyte Biology 66(5):858-866, 1999.

Vincent et al. (2005) "In Vitro Susceptibility of Macrophages to Porcine Reproductive and Respiratory Syndrome Virus Varies Between Genetically Diverse Lines of Pigs," *Viral Immunol.* 18(3):506-512.

Weingartl et al. (2002) "Continuous Porcine Cell Lines Developed from Alveolar Macrophages. Partial Characterization and Virus Susceptibility," *J. Virol. Meth.* 104(2):203-216.

(56) References Cited

OTHER PUBLICATIONS

Wensvoort et al. (Jul. 1992) "Mystery Swine Disease in the Netherlands: The Isolation of Lelystad Virus," *Vet. Quarterly* 13(3):121-130.

Wissink et al. (2003) "Identification of Porcine Alveolar Macrophage Glycoproteins Involved in Infection of Porcine Respiratory and Reproductive Syndrome Virus," *Arch. Virol.* 148(1):177-187.

Written Opinion, Corresponding to International Application No. PCT/US08/50908, Mailed Sep. 12, 2008.

Yoon et al. (1992) "Isolation of a Cytopathic Virus from Weak Pigs on Farms with a History of Swine Infertility and Respiratory Syndrome," *J. Vet. Diagn. Invest.* 4:139-143.

Zarkower et al. (1982), "Antibody-dependent cell-mediated cytotoxicity in pigs" Am J Vet Res, vol. 43, No. 9, pp. 1590-1593.

Zhang et al. (2005) "Acceleration of Endothelial-Like Cell Differentiation from CD14+ Monocytes in Vitro," *Exp. Hematol.* 33:1554-1563.

Zuckermann et al. (2001) "Characterization of Monoclonal Antibodies Assigned to the CD45 Subgroup of the Third International Swine CD Workshop," *Vet. Immunopathol.* 80:165-174.

Zuckermann et al. (2007) "Assessment of the Efficacy of Commercial Porcine Reproductive and Respiratory Syndrome Virus (PRRSV) Vaccines Based on Measurement or Serologic Response, Frequency of Gamma-IFN-Producing Cells and Virological Parameters of Protection Upon Challenge," *Vet. Microbiol.* 123:69-85.

Zuckermann et al. (Feb. 1990) "Pseudorabies Virus Glycoprotein gIII is a Major Target Antigen for Murine and Swine Virus-Specific Cytotoxic T Lymphocytes," *J. Virol.* 64(2):802-812.

Hambolu et al. (1989) "Time of Appearance of Esterase-Positive Alveolar Macrophages in Bovine Fetal Lung," Am J Vet Res 50(5):717-719.

\* cited by examiner

NON-SIMIAN CELLS FOR GROWTH OF PORCINE REPRODUCTIVE AND RESPIRATORY SYNDROME (PRRS) VIRUS

CROSS-REFERENCE TO RELATED APPLICATIONS

This application is a continuation of U.S. application Ser. No. 13/475,444 filed May 18, 2012, which is a divisional of U.S. application Ser. No. 12/013,236 filed Jan. 11, 2008, which claims benefit of application Ser. Nos. U.S. 60884782 filed Jan. 12, 2007 and U.S. 60956597 filed Aug. 17, 2007, all of which are incorporated herein by reference to the extent not inconsistent herewith.

STATEMENT ON FEDERALLY SPONSORED RESEARCH OR DEVELOPMENT

Not Applicable

BACKGROUND OF THE INVENTION

Porcine Reproductive and Respiratory Syndrome (PRRS) is a viral disease of swine that causes the greatest annual economic loss compared to any current or previous infectious disease that has ever afflicted the pork industry. PRRS, also known as "Mystery Swine Disease," Swine Infertility and Respiratory Syndrome (SIRS), and "Blue Ear Disease," was first detected in North America in 1987 and in Europe in 1990. Since then, PRRS has since become a major threat to swine industries in most pig-producing areas throughout the world, except Australia. PRRS has its most pronounced effect on young and newborn piglets. Up to 20-30% of the piglets in the litters from infected sows are stillborn, and up to 80% of piglets in infected herds die before weaning. The economic consequences of the disease, accordingly, are devastating (see U.S. Pat. No. 5,476,778 by Chladek et al.). In a study funded in part by the National Pork Board, it was noted that losses attributed to PRRS exceeded $560M in the United States alone (Neumann E J et al., 2005).

The research of PRRS and development of diagnostic and therapeutic approaches, including new vaccines and vaccine production technology, is constrained by the restricted availability of options for culturing the PRRS virus in vitro. Previously, simian cells have been the only type of available cell line known to sustain growth of PRRS for vaccine production. The simian cell line MA-104 and related derivatives (e.g., MARC-145) may represent what until now might have been the only practical option for supporting PRRS virus replication in vitro.

The present invention improves the state of the art by providing alternative options for working with PRRS virus such as the embodiment of non-simian cells that can support PRRS growth.

Other approaches have been taken, with less than desirable outcomes, to develop options for growth of PRRSV. In one approach, porcine alveolar macrophages can be used for PRRSV growth; however, the high degree of inherent variability in cells isolated from different pigs is considered a disadvantage (see Vincent et al., 2005; Bautista et al., 1993). In another approach, Weingartl et al. established porcine monomyeloid cell lines following transfection of primary porcine alveolar macrophages obtained from 12-week-old pigs. Those cells were tested but failed to support replication of PRRSV (Weingartl et al., 2002, Journal of Virological Methods 104:203-216). In contrast the present invention surprisingly discloses, inter alia, the discovery that certain cells from fetal pigs are indeed capable of supporting PRRSV growth.

Technology applications of great interest for utilization of the present invention include applied research aspects such as veterinary vaccine production in addition to the ability to study the growth of the PRRS virus at the basic research level. Vaccines for PRRSV which are modified live vaccines or inactivated killed/vaccines can be produced by the cells and cell lines of the invention. A tool to grow this particular virus and related methods also are significant in the context of generating material useful for diagnostic applications. In the context of a historical analogy intended to emphasize breakthrough science, the ability to work with human immunodeficiency virus (HIV) was generally stifled due to difficulties and a lack of options for culturing the virus in vitro. Crucial advances in the ability to study and generate diagnostics and potential vaccines for HIV related to the watershed event of being able to successfully culture the virus in vitro; see Gallo R C, 2002, Historical essay. The early years of HIV/AIDS; Science 298(5599):1728-30.

The major limitation to the control of PRRS disease is believed to rest with the availability and efficacy of vaccine technologies. The contribution of innovative cells and methods for growth of PRRS virus thus represents a significant advance in the ability to work with PRRS virus, to develop alternative and/or improved vaccine technologies, and to address the problem of PRRS disease.

SUMMARY OF THE INVENTION

The invention broadly relates to non-simian cells capable of reproducing PRRS virus and methods for reproducing PRRS virus using such cells.

In an embodiment, the invention provides an isolated non-simian cell capable of reproducing the PRRS virus, wherein the non-simian cell is obtained from an individual animal and cultured for at least 5 passages.

In an embodiment, the invention provides an isolated porcine fetal lung cell capable of infection by and/or reproducing the PRRS virus. In an embodiment, the cell is an alveolar macrophage cell. In an embodiment, the cell is propagated in culture for at least 5 passages. In an embodiment, the cell is propagated in culture for at least 10 passages. In an embodiment, the cell is propagated in culture for at least 20 and/or 50 passages.

In an embodiment, the invention provides an isolated primary cell or cell population obtained from a lung of a porcine fetus. In an embodiment, the fetus is from about 30 to about 90 days of gestational age. In an embodiment, the cell is an alveolar macrophage or the cell population comprises at least one alveolar macrophage cell. In an embodiment, the cell is a macrophage, of macrophage lineage, or progenitor thereof.

In an embodiment, the invention provides a cell or cell line designated herein as ZMAC. In an embodiment, the invention provides a cell or cell line designated herein as FBAL-A. In an embodiment, the invention provides a cell represented by a deposit with the American Type Culture Collection designated as ATCC Patent Deposit No. PTA-8764 or derived therefrom.

In an embodiment, the invention provides an immortalized cell variant or derivative of a cell described herein having the capability of supporting PRRSV growth.

In an embodiment, the invention provides a method of generating progeny of a PRRS virus comprising:

a) providing an isolated or purified non-simian cell capable of replicating a PRRS virus, wherein said non-simian cell is cultured for at least 5 passages;

b) exposing said non-simian cell to said PRRS virus; and c) allowing the PRRS virus to replicate in the cell;

thereby generating progeny of a PRRS virus. In an embodiment, the non-simian cell is obtained from an individual animal. In an embodiment, the method further comprises harvesting the grown PRRSV.

In an embodiment, the invention provides a method of producing a PRRS vaccine, comprising providing a modified-live virus (MLV) strain of PRRSV, and growing said MLV strain in an isolated or purified non-simian cell capable of replicating said PRRSV MLV strain. In an embodiment, the non-simian cell is a macrophage cell or of macrophage lineage or a progenitor thereof. In an embodiment, the non-simian cell is a porcine cell or derivative thereof. In an embodiment, the non-simian cell is a porcine alveolar macrophage cell. In an embodiment, the non-simian cell is a porcine alveolar macrophage primary cell, cell population, variant or derivative thereof. In an embodiment of the method, the cell is represented by a cell designated as ZMAC-1, FBAL-A, or a deposit with the American Type Culture Collection designated as ATCC Patent Deposit No. PTA-8764 or derived therefrom.

In an embodiment, the invention provides a composition comprising cell or cell line designated as ZMAC-1 or represented by a deposit with the American Type Culture Collection designated as ATCC Patent Deposit No. PTA-8764 or derived therefrom. In an embodiment, the invention provides a composition comprising a cell or cell line designated as FBAL-A.

In an embodiment, the invention provides a method of isolating a cell from a porcine fetal lung comprising providing a porcine fetal subject; obtaining a cell-containing bronchoalveolar lavage sample from said subject; and separating a cellular component from said sample; thereby isolating said cell. In an embodiment, said cell-containing sample is a bronchoalveolar lavage sample. In an embodiment, said sample is an excised tissue sample which is optionally processed by maceration and/or homogenization.

In an embodiment, the invention provides a method of growing a virus, comprising: (a) isolating a cell from a porcine fetal lung; (b) culturing said cell; and (c) contacting said cell with said virus so as to allow viral replication; thereby growing the virus. In an embodiment, said virus is a PRRS virus. In an embodiment, said virus is an attenuated PRRS virus or a PRRS virus field isolate. In an embodiment, the field isolate is virulent or naturally of low virulence or non-virulent. In an embodiment, said culturing comprises passaging said cell for at least 5 passages and/or growing said cell for at least 10 days of continuous culture.

In an embodiment, the invention provides a method of growing and isolating PRRSV, which comprises inoculating the virus on a culture of non-simian cells in the presence of serum in a suitable growth medium and incubating the inoculated cells until PRRSV progeny virus material is generated. In a particular embodiment, the PRRSV is ATCC-VR2332. In a particular embodiment, the non-simian cells have been previously grown in culture for at least 5 passages. In an other particular embodiment, the non-simian cells have been previously cultured for at least 10, 20, and/or 50 passages.

In an embodiment, the invention provides a method of growing PRRSV comprising (a) inoculating PRRSV on non-simian cells that have been previously cultured for at least 5, 10, 20, and/or 50 passages; and (b) incubating the inoculated non-simian cells. In an embodiment, the non-simian cells are porcine alveolar macrophages. In an embodiment, the non-simian cells are obtained from a porcine fetal lung sample. In an embodiment, the PRRSV is derived from a homogenate of swine tissue infected with the virus. In an embodiment, the method comprises incubating the culture until a fixed time period and/or until a cytopathic effect is observed. In an embodiment, the fixed time period is from about 16 to about 72 hours.

In an embodiment, the invention provides an immunogenic composition comprising inactivated PRRSV, wherein the inactivated virus is formed by a process which includes growing PRRSV on non-simian cells prior to inactivating the virus, wherein the non-simian cells have been previously cultured for at least 5, 10, 20, and/or 50 passages. In an embodiment, growing the virus comprises: (a) inoculating swine infertility and respiratory syndrome virus on the cells; and (b) incubating the inoculated cells at about 34 to about 37 degrees C. In an embodiment, growing the virus involves a growth medium including serum. In an embodiment, the inactivated virus is killed PRRSV strain ATCC VR-2332. In an embodiment, the immunogenic composition further comprises an adjuvant and/or a pharmaceutically acceptable carrier.

In an embodiment, the invention provides a composition comprising a virus grown in a cell of the invention. In an embodiment, the virus is a PRRS virus (which can include a virus derived from a PRRS virus).

In an embodiment of methods of the invention, a cell of the invention is contacted with a growth factor composition. In an embodiment, the growth factor composition comprises macrophage colony stimulating factor (MCSF). In an embodiment, the growth factor composition comprises granulocyte-macrophage colony stimulating factor (GMCSF).

In an embodiment, the invention provides a composition comprising PRRSV in or from a culture of non-simian cells; wherein the non-simian cells have been previously cultured for at least 5, 10, 20, and/or 50 passages, are derived from a porcine alveolar macrophage originating from a fetal porcine lung sample, or both. In an embodiment, the PRRSV is a fastidious, non-hemagglutinating, enveloped RNA virus and is capable of effecting PRRS in swine. In an embodiment, the composition has a virus titer of about $10^3$ to about $10^7$ $TCID_{50}$/ml. In an embodiment, the virus titer is up to about $10^9$ $TCID_{50}$/ml. In an embodiment, the PRRSV is an MLV strain. In an embodiment, the PRRSV is derived from an inoculum comprising a homogenate of tissue from a swine affected with PRRS. In an embodiment, the inoculum is derived from a neutralized tissue homogenate, and the neutralized tissue homogenate is obtained by neutralizing the tissue homogenate with antibody sera to swine diseases selected from the group consisting of hemophilus, brucellosis, leptospira, parvovirus, pseudorabies, encephalomyocarditis, enterovirus, swine influenza, and mixtures thereof. In an embodiment, the inoculum is derived from a filtered homogenate of the tissue homogenate, the filtered homogenate containing particles having a size no greater than about 0.45 micron.

In an embodiment, the invention provides a non-simian cell wherein the cell is a porcine cell. In a particular embodiment, the cell is derived from a porcine lung. In a preferred embodiment, the cell is derived from a porcine fetal lung. In a particular embodiment, the porcine fetal lung is from a porcine fetus of a gestational age from about 20 to about 80 days. In a particularly preferred embodiment, the porcine fetus has a gestational age of from about 50 to about 70 days. In an embodiment, the cell is obtained from a lung lavage sample from a porcine fetus. In a particular embodiment, the cell is a porcine alveolar macrophage cell.

In an embodiment, nonadherent and/or relatively less adherent cells are preferably selected. In an embodiment, a mixed cell population is obtained from a porcine fetal lung. In an embodiment, there are at least two cell types in the mixed cell population including a precursor cell of macrophage/monocyte lineage which is self-renewing and relatively less differentiated or undifferentiated; and a differentiated cell of macrophage/monocyte lineage which is relatively more differentiated. In an embodiment, there is at least a third cell type in the mixed cell population which is a feeder/helper cell type. In an embodiment, the third cell type is either from an endogenous sample or is added exogenously.

In an embodiment, a cell and/or cell population of the invention can be described as having a population of precursors of endothelial cells that can be made to produce endothelial cells under appropriate culture conditions. For example, the culture conditions can include the type of plasticware and/or surface treatments.

In an embodiment, there can be a fraction of cells that express CD90 and CD117. In a particular embodiment, the fraction is about 30% or at least 30%.

In an embodiment, a non-simian cell of the invention is used to produce a vaccine against Porcine Reproductive and Respiratory Syndrome Virus (PRRSV).

In an embodiment, a cell or cell line of the invention is capable of supporting growth of a PRRS virus which is a wild-type virus or a laboratory strain. In a preferred embodiment the invention supports growth of a PRRS modified live virus. In a particular embodiment, the virus is a strain corresponding to or derived from a Boehringer Ingelheim product lines such as Ingelvac® PRRS and ReproCyc® PRRS swine vaccines. In a particular embodiment, the virus is a strain corresponding to or derived from a Schering-Plough product line of Prime-Pac® PRRS vaccine. In a particular embodiment, the virus is an isolate used in United States Veterinary Biological Product License (Mar. 29, 1996) for Porcine Reproductive and Respiratory Syndrome Vaccine, Reproductive Form, Killed Virus, Code 19S5.20. In an embodiment, the PRRS virus is an attenuated virus. In an embodiment, the PRRS virus is a field isolate. In an embodiment, the field isolate is a virulent strain or a strain of naturally low virulence or non-virulent. In an embodiment, compositions or methods of the invention are applicable for growth of PRRS virus material which is used for manufacture of live, attenuated, or inactivated vaccine.

In an embodiment of a cell or cell line of the invention, an immortalized derivative is established from starting material of a non-immortalized or already immortalized cell or cell line. In an embodiment, an immortalized cell line or cell line is established using one or more transformation or other immortalization techniques as is understood in the art.

In an embodiment of a cell or cell line of the invention, one or more subclones are established. For example, a subclone is isolated and reproduced according to conventional techniques such as by limiting dilution in culture.

In an embodiment of the invention, a primary cell or cell line is cultured for at least 5 passages. In other embodiments, a primary cell or cell line is cultured for at least 10 passages, at least 20 passages, and/or at least 50 passages. In an embodiment of the invention, a primary cell or cell line is cultured for at least one week. In an embodiment of the invention, a primary cell or cell line is cultured for at least two weeks. In other embodiments, a primary cell or cell line is cultured for at least four weeks, at least eight weeks, and/or at least sixteen weeks.

In an embodiment, a composition such as a cell or cell line is isolated or purified.

In an embodiment, the invention provides a process for growing a porcine reproductive and respiratory syndrome virus (PRRSV) by growing the virus in a tissue culture to an amount sufficient to protect animals against PRRS to diagnose PRRS or to identify the molecular structure of PRRSV for subunit or recombinant products, comprising inoculating PRRSV onto a tissue culture of a non-simian cell or cell line and harvesting the grown virus. In an embodiment, the cell or cell line is porcine. In an embodiment, the cell or cell line is a porcine alveolar macrophage. In an embodiment, the invention provides a tissue culture containing the PRRSV produced according to the process. In an embodiment, the invention provides a process for preparing an effective vaccine for protecting pigs against PRRS comprising providing PRRSV as described herein, releasing the PRRSV from the tissue culture cells and adjusting antigenic mass by dilution, concentration or extraction to produce an immunologically effective amount of the antigenic mass for a relatively intact, subunit, or recombinant product.

In an embodiment, a non-simian cell or cell line of the invention is used to produce live PRRSV or inactivated/killed PRRSV.

In an embodiment, the invention provides a purified non-simian cell or cell line of macrophage lineage derived from a fetal porcine organism. In an embodiment, the invention provides a method of generating a purified non-simian cell or cell line of macrophage lineage derived from a fetal porcine organism. In an embodiment, the cell or cell line is cultured in vitro for at least three, five, or 10 passages.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE FIGURES

FIG. 3B and FIG. 3C illustrate the actual morphology of fresh cells stained for CD14 or CD172 with characteristic filopodia and lamellipodia.

DETAILED DESCRIPTION OF THE INVENTION

Figure 1:
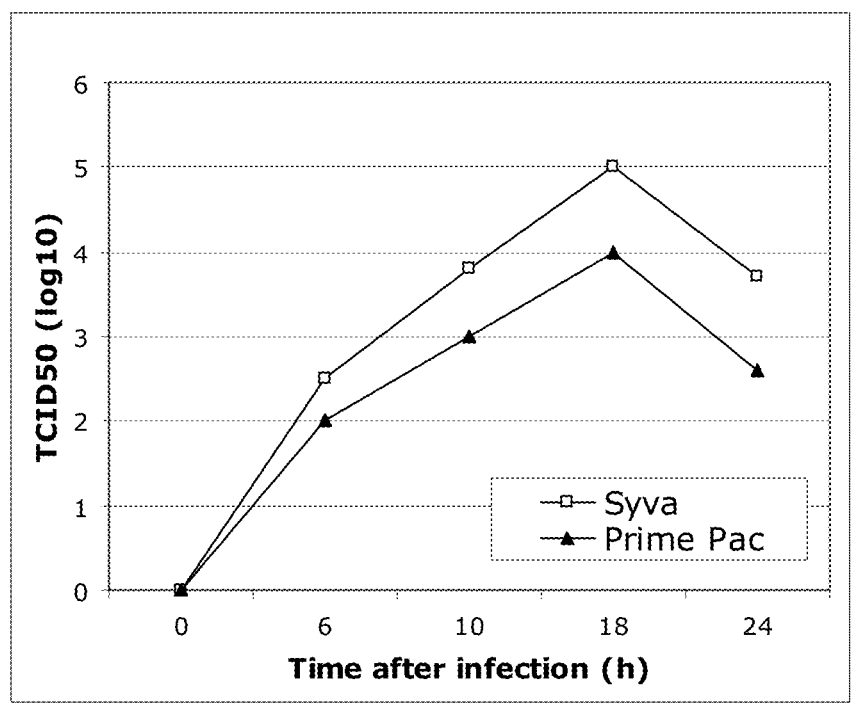
FIG. 1 illustrates the growth of two PRRSV attenuated strains (PrimePac and Syva) in a culture of non-simian cell UIMAC FBAL-A.

The following abbreviations are applicable: PRRS, Porcine Reproductive and Respiratory Syndrome; PRRSV, PRRS Virus; $TCID_{50}$, tissue culture infectious dose 50% level; ATCC, American Type Culture Collection; MOI, multiplicity of infection.

In general the terms and phrases used herein have their art-recognized meaning, which can be found by reference to standard texts, journal references and contexts known to those skilled in the art. The following definitions are provided to clarify their specific use in the context of the invention.

When used herein, the term "cell" can refer to a biological entity as would be understood in the art and which is intended to encompass specific entities that may be described as a primary cell or a cell line. When several of these terms are used herein, it will be appreciated by one of ordinary skill that such usage is merely for purposes of emphasizing well understood distinctions. For example, the phrase "a cell or cell line" may emphasize the contrast between an original primary isolate versus an immortalized version which could be a direct derivative of the original primary isolate.

When used herein, the term "isolated" refers to a manipulated state that is different than that which is the natural state and/or is modified relative to a starting material, in which case the term is meant to be consistent with the concept of being purified. For example, an isolated primary cell is excised from a natural tissue or other source in a host organism and maintained apart from the original source. As another example, a cell component can be placed in culture or further separated from a lung lavage fluid-based sample, thus achieving a relatively isolated cell.

When used herein, the term "purified" refers to a condition wherein there has been a relative enrichment, separation, and/or removal of a substance relative to a starting material. The term can encompass conditions of an at least partial purification and does not necessarily imply an absolute state of purity. For example, the term can apply to a cell that is capable of reproducing a PRRS virus and present in a mixed culture and independently can be applicable to what may customarily be considered a pure culture. The term can apply to a primary cell culture which is optionally a mixed culture. The term can apply to a cell line.

In an embodiment, the invention provides a porcine alveolar macrophage cell line which is capable of supporting the growth of PRRSV. An exemplary composition of the invention is a non-simian cell line. Particular compositions of the invention include a cell or cell population obtained from porcine fetal lung samples. A further specific composition includes a fetal porcine alveolar macrophage. In an embodiment, the invention provides methods of growing PRRSV in a non-simian cell or cell line.

The invention may be further understood by the following non-limiting examples.

EXAMPLE 1

The Non-Simian Cell Isolate UIMAC FBAL-A is Capable of Supporting PRRSV Growth

The porcine alveolar macrophage cell line UIMAC FBAL-A was derived from the lung of a 45 day old porcine fetus by bronchoalveolar lavage with culture medium. The initial culture was expanded in vitro from the initial few thousands of cells to several million over a period of 6 months. At that time, experiments were conducted to measure the growth of PRRS virus. These experiments showed that the FBAL-A cells were able to support the replication of the virus. This isolate was not deliberately transformed yet demonstrated an ability to grow and propagate in culture and a phenotype for the ability to support infectivity and growth of PRRS virus.

The cell culture conditions were as follows. Culture medium: RPMI 1640 supplemented with L-glutamine and 25 mM HEPES. The medium is supplemented with non-essential amino acids, sodium pyruvate, gentamicin, and 10% fetal bovine serum. Cells were incubated at 37° C. with 5% $CO_2$ at 100% humidity. Tissue culture grade 6 well plates were used for the culture surface. A culture volume of 4-6 ml of culture medium/well was used. For passages, cells were selected for being non-adherent or weakly adherent. Every 3-4 days a portion of the cells were removed from the culture with the aid of a Pasteur pipette and a rubber bulb by gentle suspending the cells in the culture fluid and transferring ⅓ of the well volume to a new well. The new well and the source well were fed with fresh medium.

FIG. 1 illustrates the growth of PRRSV attenuated strains PrimePac and Syva in UIMAC FBAL-A. The results demonstrate that the porcine cells can be used to produce PRRS vaccine virus in quantities sufficient for vaccine production.

The isolated porcine cells can be identified and/or isolated by expression of certain surface molecules. The surface molecule pattern of expression can be used to isolate other independent porcine cells or to screen cell lines as potential indicators for the capability of supporting PRRSV growth. For instance, cells are optionally screened for CD163 expression. In a particular example, cells or cell lines are subjected to staining and/or separation techniques by virtue of cell surface molecules.

Figure 2:
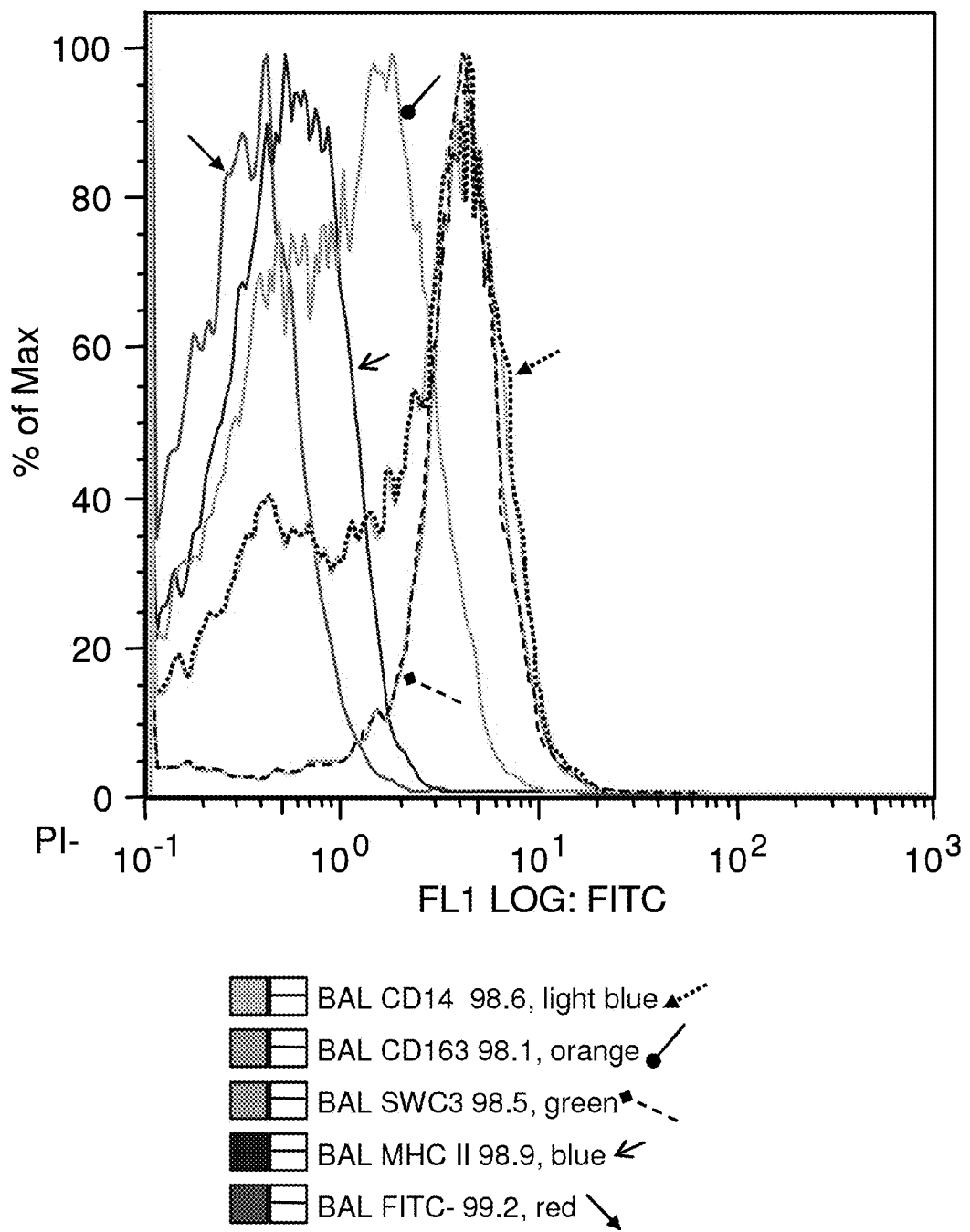
FIG. 2 illustrates the phenotype of UIMAC-FBAL-A cells including the expression of characteristic macrophage cell surface markers.

FIG. 2 illustrates the phenotype of UIMAC-FBAL-A cells including the expression of characteristic macrophage cell surface markers. The FBAL-A cells express CD14, CD163, and CD172. The protein molecule CD163 is indicative of monocyte/macrophage lineage and correlates with permissiveness of infection by African swine fever virus. The cells also express MHC class II molecules at low level. The red line towards the left side represents the staining results of the negative control sample. It is noted that expression of certain marker, including such described herein, can be used for characterization of the cells, but independently can also be used for enrichment, separation (e.g., by sorting), and other purposes. In an embodiment, a cell such as a macrophage cell of the invention may not necessarily express one or more given certain markers, or its expression pattern may change over time, but may nonetheless be capable of replicating PRRSV.

Figure 3:
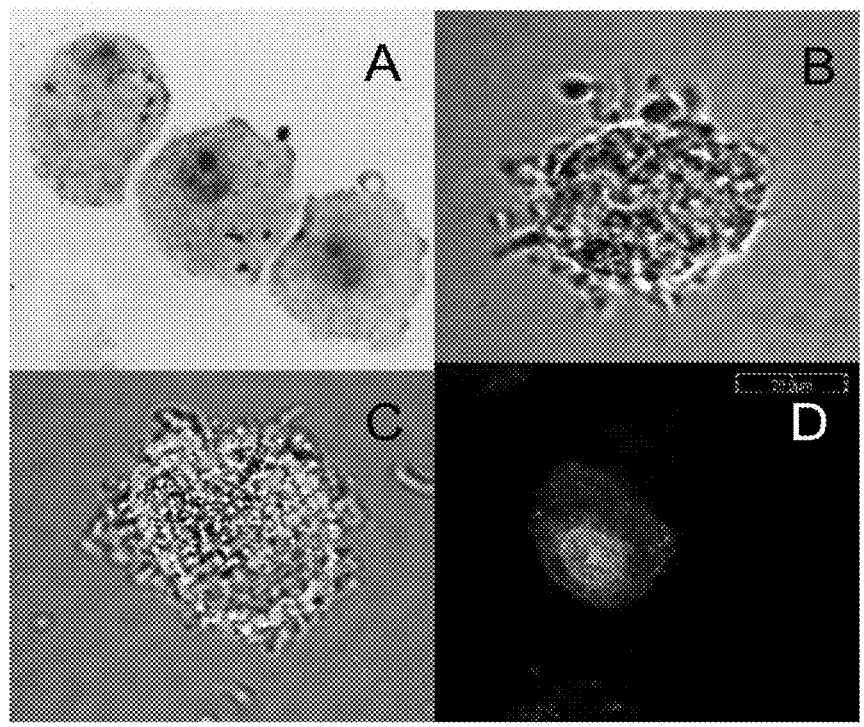
FIG. 3 illustrates morphological features of FBAL-A cells using microscopy techniques: A) Giemsa stain to show morphological appearance (cytospin); B) Confocal microscopy of FBAL-A stained for CD14; C) Confocal fluorescence microscopy staining for CD172; and D) Staining of FBAL-A infected with PRRSV staining for nucleocapside antigen which indicates a characteristic localization of N antigen to nucleus and association with nucleolus.

FIG. 3 illustrates morphological features of FBAL-A cells using microscopy techniques: A) Giemsa stain to show morphological appearance (cytospin); B) Confocal microscopy of FBAL-A stained for CD14; C) Confocal fluorescence microscopy staining for CD172; and D) Staining of FBAL-A infected with PRRSV staining for nucleocapside antigen which indicates a characteristic localization of N antigen to nucleus and association with nucleolus. FIG. 3B and FIG. 3C illustrate the actual morphology of fresh cells stained for CD14 or CD172 with characteristic filopodia and lamellipodia.

In microscopic examination experiments, cells were centrifuged onto a slide and stained with Giemsa stain. Unfixed cells were incubated with monoclonal antibody specific for SWC3 or CD14 followed by exposure to FITC-labeled goat anti-mouse Ig. For PRRSV nucleocapsid detection, cells were infected with PRRS virus (strain VR-2332). After 18 h, the cells were centrifuged onto a slide, fixed with acetone, and incubated with FITC-labeled anti-PRRS virus N protein mAb SDOW17. Uninfected cells did not react with mAb SDOW17. In growth kinetic studies, PRRSV isolate VR2332 was used in UIMAC-FBAL-A cells. Virus yields obtained from the macrophage cell line were titrated in MARC-145 cells.

Without wishing to be bound by theoretical explanation, for certain compositions it is believed that cells described herein derived from porcine fetal lungs can contain self-regenerating progenitors. These self-regenerating progenitors can produce progeny macrophages, which can further differentiate, and moreover can have the ability to produce additional progenitor cells allowing continuing propagation.

EXAMPLE 2

The Non-Simian Cell Isolate ZMAC is Capable of Supporting PRRSV Growth

In addition to the development of FBAL-A cells, an independent effort resulted in the development of a second cell isolate designated as ZMAC. ZMAC cells were characterized and observed to have the capability of supporting PRRSV infectivity and growth.

In this independent attempt, six 58 day-old fetuses were aseptically harvested from the uterus of sow 9688 obtained from the swine herd of the University of Illinois Veterinary Medicine Research Farm. This sow was a cross-bred pig with the following breed composition: 17/32 Landrace, 13/32 Yorkshire and 2/32 Duroc. The fetuses were transported to the cell culture laboratory and their lungs dissected inside of a bio-safety cabinet under sterile conditions.

Cells in the airways of the lungs from each of the 6 fetuses were isolated separately by bronchoalveolar lavage. Approximately 100,000 cells were obtained from the lung of each fetus. The cells from each fetus were cultured separately in different wells of a 6-well tissue culture plate. After an initial 4-day culture, the cells were purified via a Ficoll-Hypaque density gradient. In an embodiment, cells can be purified by Ficoll-Hypaque either the day of isolation or at a later time, e.g., 1, 2, or 3 weeks later, it is recognized that this can facilitate removal of certain components such as red cells, and potentially other material, present in an original preparation). Within 20 days after establishment of the initial cultures, the cells were exhibiting robust growth and were split into additional 6-well plates. These cells were named ZMAC/FBAL-II and further designated as sublines 1-6 to identify the cells isolated from the 6 different fetuses. Subsequently the cells were split approximately every 4-5 days. The robust growth of cells was evident by the presence of cell clusters which started to double in terms of cells per cluster about every 2.5 to 3 days. By 60 days after the initiation of the culture, the ZMAC/FBAL-II.1, and ZMAC/FBAL-II.2 cells exhibited better growth than the other four lines. Upon further passages, the ZMAC/FBAL-II.1, and ZMAC/FBAL-II.2 lines were growing sufficiently well to be transferred to 75 cm$^2$ tissue culture flasks. Culture conditions were generally as described above. In this experiment, Sarstedt flasks for suspension cultures were used.

Upon multiple passages, the cells exhibited vigorous growth; several million cells were able to be harvested every 10-12 days. Growth curves indicated that the cells are capable of replicating PRRS virus as well as the FBAL-1 (FBAL-A) cells. In one assay, the yield of virus was approximately 0.2 TCID$_{50}$/cell. Two types of modified live PRRS virus isolates were tested for growth in these cells (PrimePac strain of Schering-Plough and the Spanish vaccine isolate of Syva in Europe).

Five lots of cells were frozen and stored in liquid nitrogen. Each lot has a minimum of 10 vials with two million cells each. A representative vial from each lot was found to have >80% viability after being thawed and to exhibit vigorous growth within 4 days after culture initiation. The ZMAC population has been found to be 70% susceptible to infection with PRRS virus as determined immunofluorescence staining for viral proteins within 18 hours after infection at an MOI of 0.01. In another assessment, we determined that the ZMAC cell line is 100% susceptible to infection by PRRS virus, as determined by immunofluorescence staining for viral proteins 12 hours after infection at an MOI of 10.

We have also performed multiple step growth curves by infecting the ZMAC cells with PRRS virus (PrimePac) at an MOI of 0.02. Based on real time PCR analysis of virus genome expression in the infected cells and by titrating the amount of virus progeny produced, we have determined that the first round of replication of PRRS virus is completed by 9 hours after infection, and that the peak yield of virus progeny is achieved by the second round of replication at 18 hours after infection (FIG. 4B).

Figure 4:
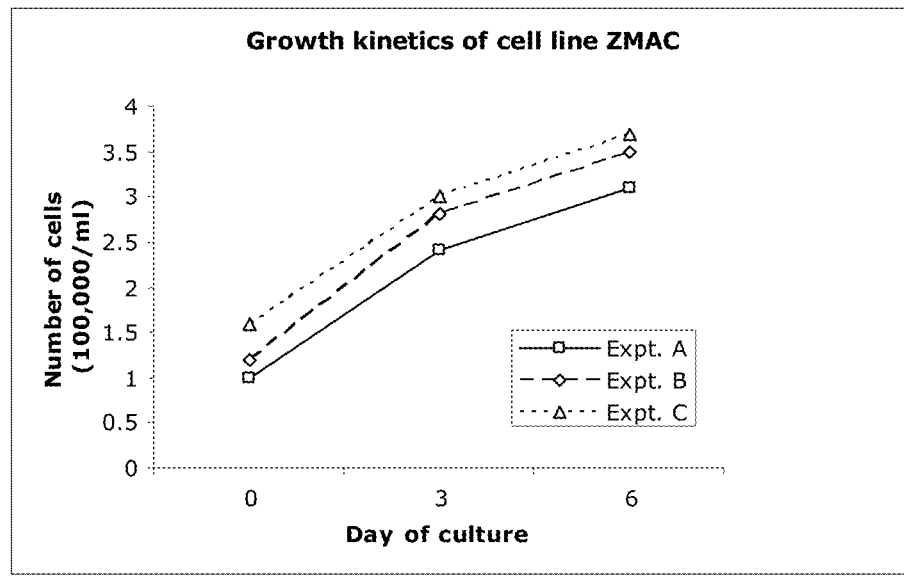
FIG. 4 illustrates data on growth kinetics of the ZMAC cells (FIG. 4A) and PPRSV growth using the cells (FIG. 4B).
Figure 4:
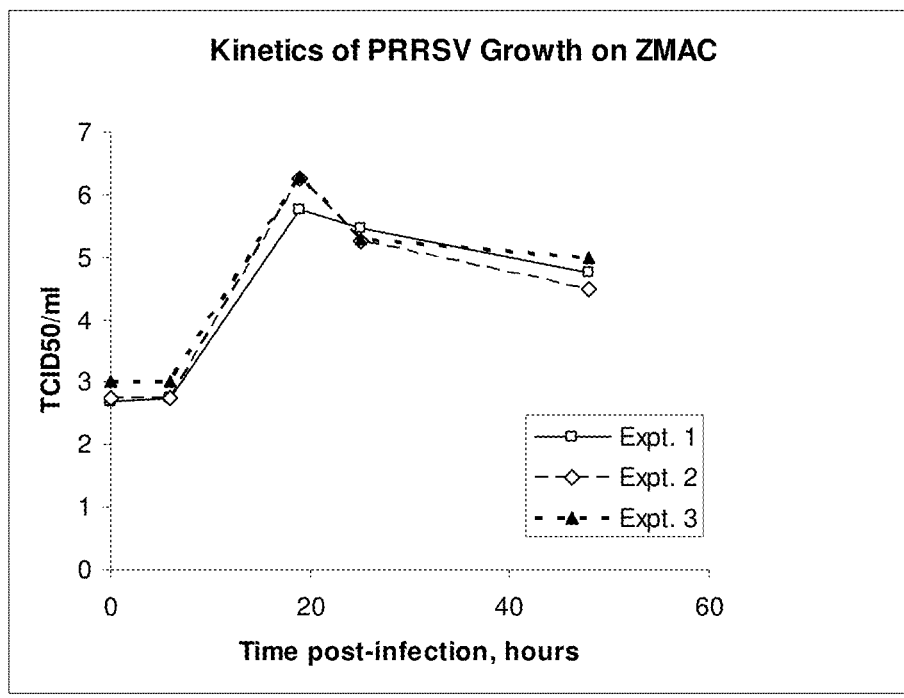

In FIG. 4, FIG. 4A shows results of growth kinetics of the ZMAC cells. Established cultures of ZMAC cells were grown in 75 cm$^2$ culture flasks containing 15 ml of cells at 2-3.2×10$^5$ cells/ml; cells were fed with an equal volume of fresh culture medium to achieve a cell density of 1-1.6×10$^5$ cells/ml. Cells were counted at 0, 3, and 6 days after fresh medium was provided. Each flask is capable of producing 2-3×10$^6$ cells every four days.

FIG. 4B illustrates a multiple step growth curve of PRRS virus on ZMAC cells. In these experiments, the results indicate the viral yields and kinetics of PRRSV growth on ZMAC cells. A suspension of ZMAC cells at 1×10$^6$/ml were infected at an MOI of 0.02 with attenuated PRRS virus isolate Prime-Pac. After one-hour incubation at 37 C. the inoculum was removed by centrifugation, and the cells were suspended at 1×10$^6$/ml. A 0.1 ml volume was removed at the indicated times after infection and the number of TCID$_{50}$ units determined in MARC-145 cells. The attenuated PRRS virus strain PrimePac, potentially suitable as a vaccine material, grows well in the ZMAC cell line.

Figure 5:
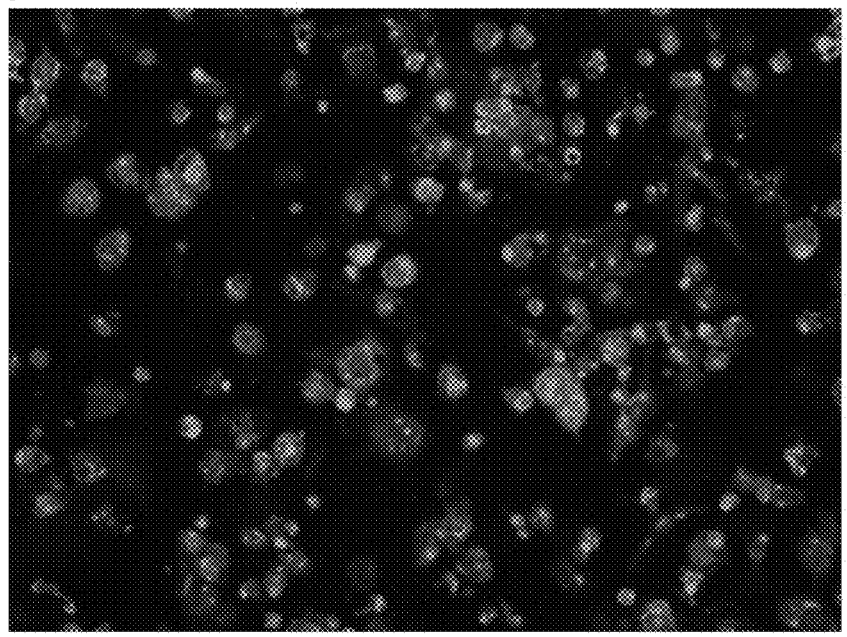
FIG. 5 illustrates ZMAC cells at 20 hours after being infected with PRRS virus strain NADC20 at MOI of 1 (FIG. 5A) and 0.1 (FIG. 5B). Cells were fixed and stained with FITC labeled SDOW17 mAb that is specific for the nucleocapsid (N) protein.
Figure 5:
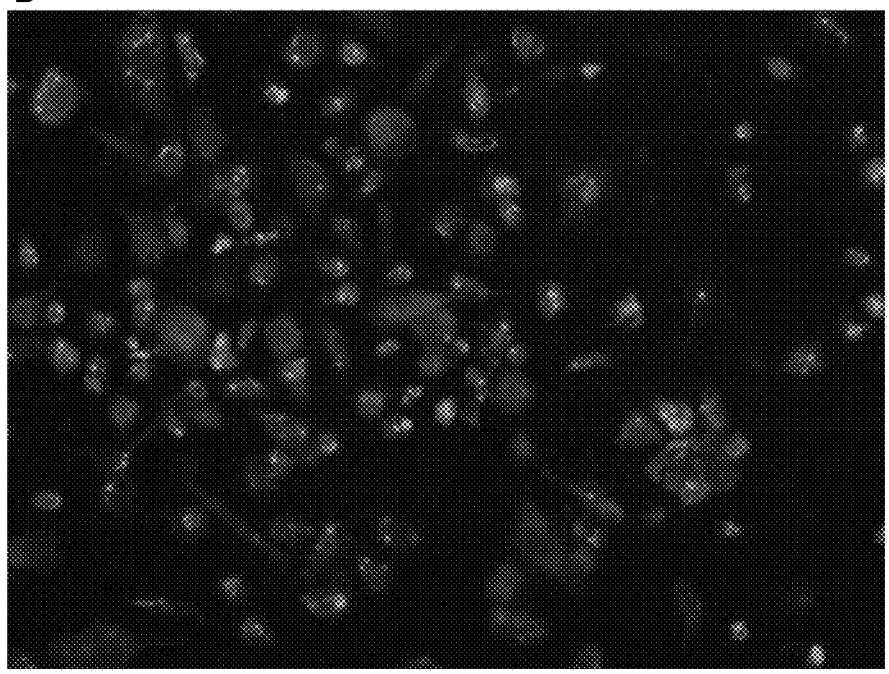
Figure 6:
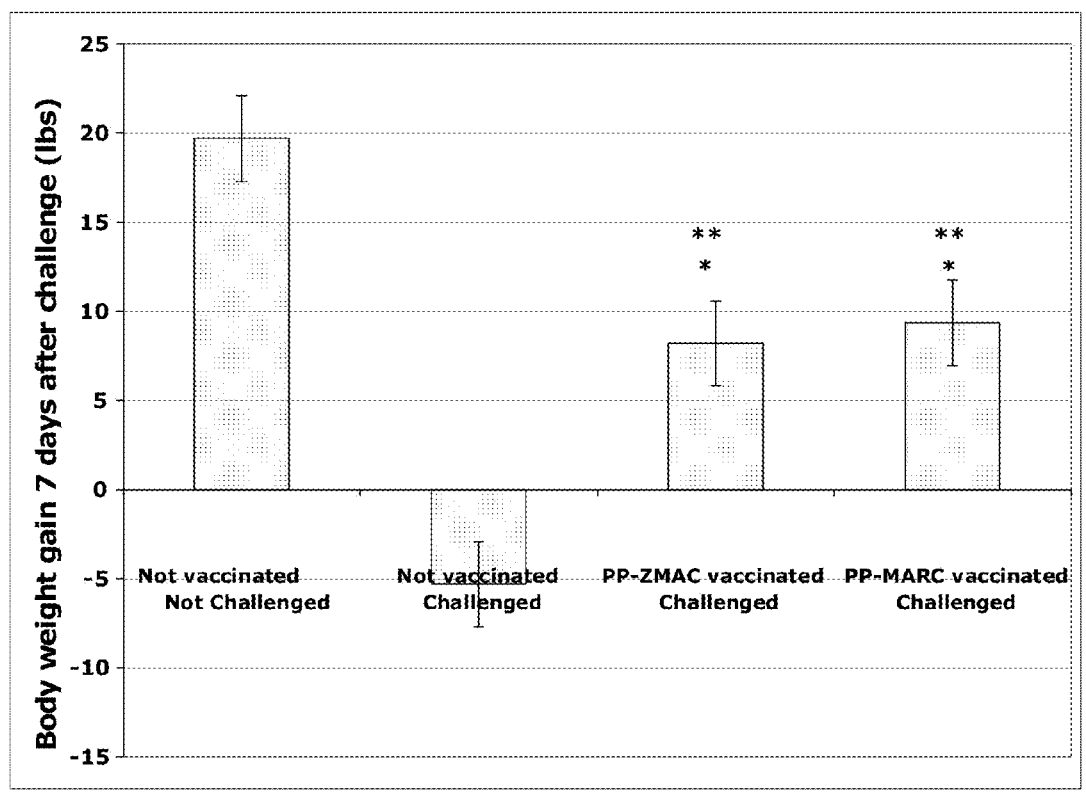
FIG. 6 illustrates results of weight change in pigs after exposure to wild-type PRRS virus.
Figure 7:
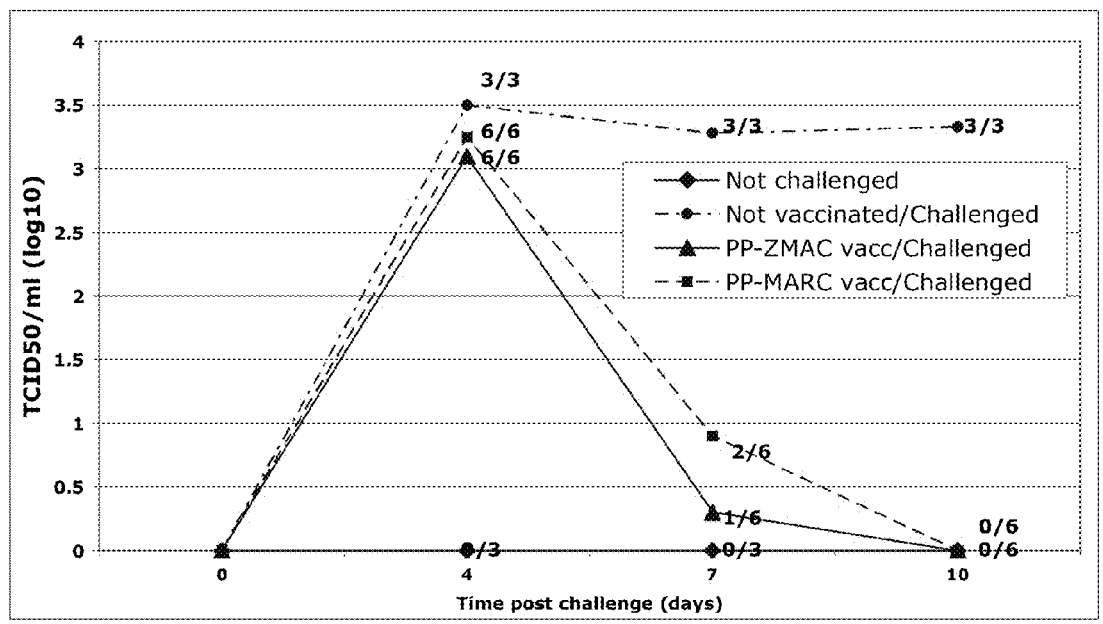
FIG. 7 illustrates the extent and frequency of viremia in pigs after exposure to wild-type PRRS virus.
Figure 8:
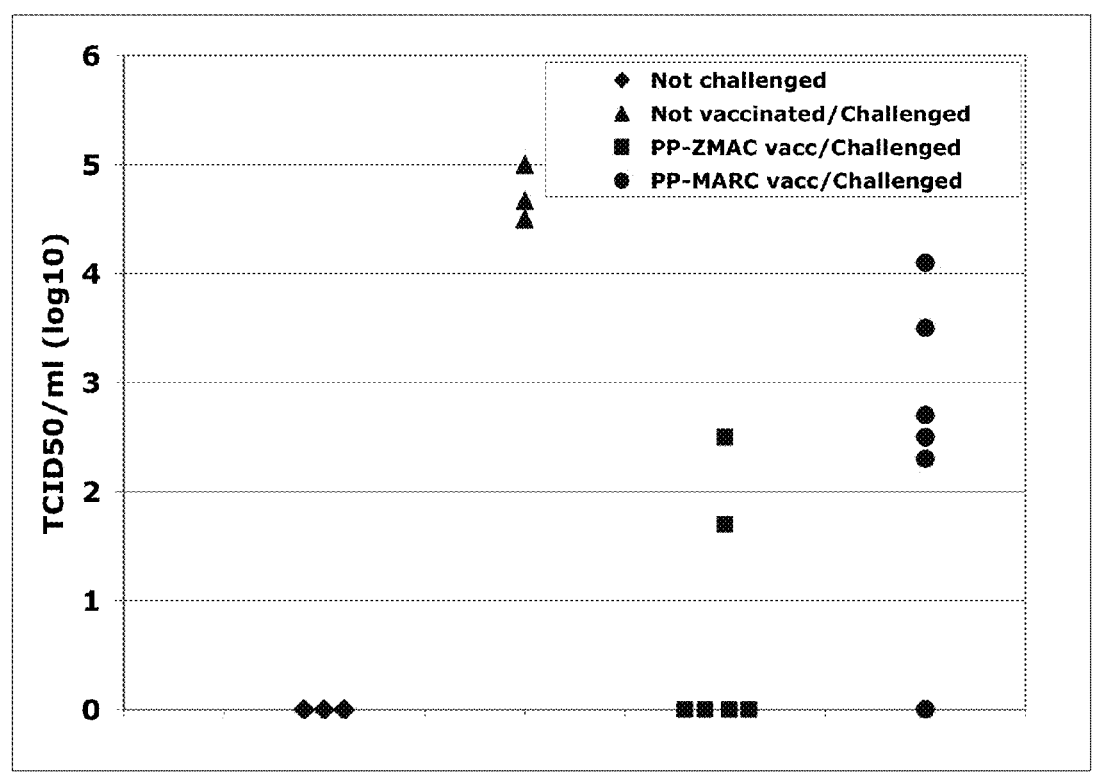
FIG. 8 illustrates results of measuring virus load in samples from the bronchalveolar lavage of pigs after exposure to wild-type PRRS virus.

FIG. 5 illustrates ZMAC cells at 20 hours after being infected with PRRS virus strain NADC20 at an MOI of 1 (FIG. 5A) and 0.1 (FIG. 5B). A negative control with mock infected cells was also observed (not shown). Cells were fixed and stained with FITC labeled SDOW17 mAb that is specific for the nucleocapsid (N) protein. Phase contrast microscopy was also performed to observe the cells. Generally these cells do not show CPE until about 28-36 hours after infection. A substantial amount of virus material, however, is released from the cells much earlier, for example by about 18-20 hours after infection.

Samples of cells are used to adapt cell growth conditions and viral growth conditions for purposes of maximizing and/or optimizing virus titers. PRRS viral stocks are generated accordingly and can be used for vaccine development and vaccination purposes.

EXAMPLE 3

Immortalized Non-Simian Cell Lines Capable of Supporting PRRSV Growth

A cell or cell line of the invention is established as one or more of a spontaneous immortalized variant, deliberately transformed derivative, other variant or derivative, and an otherwise immortalized version of a primary cell or cell line as described herein.

For instance, techniques are utilized as would be understood in the art, such as involving viral transformation technology; fusion with an immortalized partner; exposure to chemical/physical conditions including; e.g., irradiation; and technology relating to manipulation of telomerase function. In a preferred approach, the tert system is used to establish a cell or cell line which can avoid, delay, or otherwise alter senescence. See, e.g., Carrillo et al., Veterinary Immunology and Immunopathology 89 (2002) 91-98; Kwak S et al., 2006 Animal Biotechnology, 17: 51-58; http://www.atcc.org/common/products/CellImmortProducts.cfm.

In preliminary isolation efforts or downstream development of an immortalized cell, aspects such as purification and/or subcloning are facilitated by fluorescence activated cell sorting or other flow cytometry separation or analysis technique. Other techniques such as magnetic cell separation are adaptable for use with cells and methods herein.

EXAMPLE 4

Determination of Immunogenicity and Efficacy of a PRRS Modified Live Vaccine

In this example, the immunogenicity and efficacy of a PRRS modified live virus vaccine produced using a porcine macrophage cell line is determined. A porcine alveolar macrophage cell line is tested. In a particular instance, the porcine macrophage primary cell lines UIMAC-FBAL-A and/or ZMAC are used. Alternatively, one can generate independent starting materials and/or derivatives such as transformants according to the disclosure herein.

A PRRS MLV candidate is selected and produced in connection with a cell or cell line as described herein to generate PRRS MLV material for clinical trial evaluation. A vaccination and challenge study is conducted with 32 pigs that are four weeks of age, randomly allocated into four groups of n=8 per group. The pigs are obtained from the University of Illinois Veterinary Research Farm PRRS virus-free swine herd and acclimated at an isolation facility for one week before starting the study.

Animals in groups 1 and 2 are immunized once in the rump area with a dose of $5\times10^4$ $TCID_{50}$ units in a 2 ml volume of the MLV stock grown in either the UIMAC-FBAL-A cells or in MARC-145 cells. Animals in group 3 are injected with a 50:50 mixture of 2 ml of spent culture supernatant from UIMAC-FBAL-A and simian MARC-145 cells. The animals in group 4 are not treated and serve as controls. As a measurement of virus-specific immunity, peripheral blood samples are collected from each animal at weeks 0, 2, 4, 6 and 8 weeks post-immunization. From these samples, serum and PBMC are obtained and the intensity of the humoral and cell-mediated immune responses measured. The titer of serum virus-neutralizing antibodies and the frequency of PRRS virus-specific interferon (IFN)-gamma-secreting sells (SC) separately against the two parental PRRS virus isolates FL-12 and NEB-1, a chimeric virus (Kwon B, 2006), and virulent challenge strain VR2385 (Opriessnig T, 2002). To measure the level of protective immunity induced by the vaccine material, animals in groups 1-3 are challenged at 6 weeks post-immunization by instillation of 2 ml of the virulent PRRS virus strain VR2385 ($10^5$ $TCID_{50}$ doses per 2 ml, administered in aliquots of 1 ml per nostril). Animals in group 4 remain unvaccinated and are not challenged in order to determine normal clinical parameters as well as normal lung appearance. The PRRS virus-naïve animals in group 3 will serve as the challenge controls to determine the severity of the challenge. The degree of protective immunity elicited by the vaccine is established based on factors including the measurement of body temperature and weight change and the observance of clinical signs such as depression and respiratory signs. These parameters are monitored daily for fourteen days. The level of viremia, IFN-gamma response, and body weight are determined at 0, 4, 7, 10 and 14 days post-challenge. Fourteen days after challenge, the animals are euthanized, and the viral load in lung tissue and bronchoalveolar lavage fluid determined. Pathological changes in the lung are assessed at the macro and microscopic levels.

In another experiment, the immunogenicity and efficacy of biologic material generated from ZMAC is evaluated. The ZMAC material is compared to the same vaccine virus but grown in the MARC-145 cells. For this purpose we have performed 3 serial passages of the PrimePac virus strain in ZMAC cells. The third passage of this virus in the ZMAC cells is utilized to conduct the comparative vaccination study of this biologic to the PrimePac virus grown in MARC-145 cells. Stocks of the PrimePac vaccine grown in either the ZMAC or MARC-145 cells are prepared to a titer of $10^6$ $TCID_{50}$/ml. Groups of pigs are immunized at $5\times10^4$ TCID50 dose in a 2 ml volume of the MLV stock grown in either the UIMAC-FBAL-A cells or in MARC-145 cells.

EXAMPLE 5

Use of a Porcine Alveolar Macrophage Cell Line to Produce a PRRS Modified Live Virus Vaccine Introduction. In mid-1994, the first PRRS MLV vaccine (Ingelvac PRRS MLV) was released. Since then, the use of attenuated viruses as vaccines has become customary in North America and Europe. It is well accepted that these agents are effective in conferring appropriate levels of homologous protective immunity while affording variable degrees of protection against challenge by heterologous strains (Mengeling et al., 1996; Mengeling et al., 1999). Thus there is motivation and interest directed for further progress in technologies of alternative and improved strategies, vaccines, and tools and methods in connection therewith.

In this study, a porcine alveolar macrophage cell line, designated ZMAC-1, is used for the production of a PRRS modified live virus (MLV) vaccine. Also, the efficacy of vaccine virus grown in this porcine host is compared to that propagated in the only other cell line known at the initiation of this study to support the growth of PRRS virus, namely the simian cell line MA-104 and/or its derivative the MARC-145 line.

Initially, the ZMAC-1 cells were found to be readily susceptible to the MLV vaccine Prime Pac PRRS (Schering-Plough Animal Health). Moreover, after the third passage of the virus in ZMAC-1 cells, a yield comparable to that achieved when using MARC-145 cells was obtained. To evaluate the vaccine potential of both ZMAC-1 cell-grown virus, a standard immunization-challenge study was conducted. In this case, six 8 week-old pigs were injected with an equivalent dose of the Prime Pac vaccine grown in either ZMAC-1 or MARC-145 cells while two additional groups of three animals were not immunized. Four weeks later, all vaccinated and one of the PRRS virus-naïve groups were challenged with the "atypical PRRS abortion storm" virus isolate NADC-20. One outcome of the study was that the Prime Pac MLV vaccine grown in either cell line was equally effective at preventing the body weight loss of PRRS virus-naïve pigs that had been exposed to the heterologous virus 7 days earlier. However, the vaccine virus grown in ZMAC-1 cells was significantly more effective than that grown in MARC-145 at reducing the extent of viremia and also at eliminating virulent virus from the lungs at 7 and 10 days post-challenge, respectively.

The observation that the type of cell line used to grow the PRRS MLV vaccine can improve the level of protective immunity elicited by the same vaccine virus against a genetically divergent virulent PRRS virus has important implications for the prospect of developing a highly effective vaccine against this pathogen. Namely, the results of this study suggest that the effectiveness of a PRRS MLV virus vaccine is not, as it is commonly believed, only determined by its genetic similarity to the challenge virus, but is also influenced by how it is produced. The results of this study are significant in demonstrating that porcine cells are useful in generating an effective MLV vaccine against PRRS virus.

Abstract. A porcine alveolar macrophage cell line, designated ZMAC-1, was generated and its utility to manufacture an effective PRRS modified live virus (MLV) vaccine was examined. This cell line was found to be 100% susceptible to infection by PRRS virus, as evidenced by the successful immunofluorescence staining for viral proteins at 20 hr after infection. Moreover, based on multiple step growth curve analyses, the first round of PRRS virus replication was determined to be completed by 9 hr after infection and the yield of virus progeny during the second round of replication at 19 hr after infection.

To compare the efficacy of stocks of the MLV vaccine Prime Pac PRRS (Schering-Plough Animal Health) prepared in either ZMAC-1 or the simian cell line MARC-145, a standard immunization-challenge study was conducted. Six 8 week-old pigs were initially vaccinated intramuscularly with an equivalent dose ($10^4$ $TCID_{50}$) of the Prime Pac vaccine grown in either ZMAC-1 or MARC-145 cells, while two additional groups of three animals were not immunized. All of these animals, as well as one of the two groups of unvaccinated controls, were challenged 4 weeks later with $10^4$ $TCID_{50}$ of the "atypical PRRS abortion storm" virus isolate NADC-20. While the unvaccinated animals experienced an average body weight (BW) loss of $-5\pm4$ lb by 7 days after the virulent virus challenge, the PRRS virus-naïve controls had gained on average $19.7\pm6$ lb during this time interval. In contrast, at 7 days post-challenge, the animals vaccinated with the MLV virus grown in either ZMAC-1 or MARC-145 cells exhibit average BW gains of $8.2\pm5.2$ and $9.3\pm3.6$, respectively. Thus, statistically the Prime Pac MLV vaccine grown in either cell line was equally effective at reducing the negative effect of the exposure of pigs to a highly virulent PRRS virus on their growth. Remarkably, analyses of the virus load in serum and lung lavage samples from PRRS virus-immunized and challenged animals revealed that the vaccine virus grown in ZMAC-1 cells was significantly ($P=0.015$) more effective at reducing the extent of viremia at 7 days post-challenge and also at eliminating virulent virus from their lungs by 10 days post-challenge. The observation that the type of cell line used to grow the PRRS MLV vaccine can improve the level of protective immunity elicited by this product against a genetically divergent virulent PRRS virus has significant implications for developing a highly effective vaccine against this pathogen. Namely, the results of this study suggest that the effectiveness of a PRRS MLV virus vaccine is not only, as it is commonly believed, determined by its genetic similarity to the challenge virus, but is also influenced by how it is produced.

Objectives of this study, at least in part, included the determination of (1) the growth characteristics of attenuated PRRS virus strains in the porcine macrophage cell line ZMAC-1; and (2) the immunogencity and efficacy of a PRRS modified live virus vaccine produced in the porcine macrophage cell line ZMAC-1.

Materials and Methods

Cells. Porcine alveolar macrophage cells were selected, e.g., as further described herein, from the lung lavage of a 58 day-old fetus obtained from an SPF (specific pathogen free) sow. The cells were cultured in RPMI-1640 medium, supplemented with 10% fetal bovine serum, sodium pyruvate and non-essential amino acids, and maintained at 37° C. in a 5% $CO_2$ atmosphere. A cell line, designated ZMAC-1, was established in May of 2006 and has since been continuously growing. Stocks representative of different temporal subdivisions of this cell line have been cryo-preserved.

Virus. The MLV vaccine Prime Pac PRRS (Schering-Plough Animal Health) was sequentially passaged three times in ZMAC-1 cells. Although the titer was only $10^4$ $TCID_{50}$/ml after the first two passages, the virus appeared to have adapted during the third passage as the titer had increased to $10^{6.25}$ $TCID_{50}$/ml. Accordingly, this progeny was used for vaccination. Stocks of the Prime Pac vaccine were also prepared in MARC-145 cells as previously described (Osorio et al., 2006) and attained a titer of $10^6$ $TCID_{50}$/ml. The "atypical PRRS abortion storm" virus isolate NADC-20 (Harms et al., 2001) was grown in ZMAC-1 cells and exhibited a maximum titer of $10^{7.6}$ $TCID_{50}$/ml.

Vaccination and Challenge Study: Eighteen 8-week-old SPF pigs (free of all major swine pathogens including PRRS virus, mycoplasma and circovirus) were randomly allocated into 6 isolation cubicles (3 pigs per cubicle) at a suite in the Biocontainment Facility at the University of Illinois. Animals from four cubicles were injected once in the rump area with a 2 ml solution containing $10^4$ $TCID_{50}$ of Prime Pac virus grown in either ZMAC-1 or MARC-145 cells, for a total of 2 cubicles per vaccine formulation (6 pigs total). The six remaining pigs in the two other cubicles were not immunized and served as unvaccinated controls. Four weeks after vaccination, all of the immunized animals as well as three of the control pigs housed in one cubicle were challenged with $10^4$ $TCID_{50}$ of PRRS virus strain NADC-20. While the unvaccinated and challenged animals served to establish the severity of infection by the NADC-20 PRRS virus, the PRRS virus-naïve pigs in the remaining cubicle were used to provide normal clinical parameters of growth and health. The degree of protective immunity elicited by the vaccine was determined based on a comparison of body weight (BW) changes and the appearance of depression and respiratory signs. These parameters were monitored daily for ten days after the challenge. The level of viremia was determined at 0, 4, 7 and 10 days after challenge by measuring infectious units in MARC-145 cells. Ten days after the challenge, the animals were euthanized and the viral load in the bronchoalveolar lavage (BAL) fluid was determined by using real time PCR and virological methods as previously described (Zuckermann et al., 2007).

Statistical Analysis. Analysis of Variance was used to determine significant differences among groups of pigs in regard to weight gain. Group means were compared by Fisher's least significant difference procedure utilizing Stat View software (SAS). To minimize the effect of BW weight differences between animals at the time of challenge, the data was calculated as the difference between the BW of the animals at the time of challenge and 7 days later.

Results

Objective 1. Determine the growth characteristics of attenuated PRRS virus strains in the porcine macrophage cell line ZMAC-1. The goal of this aim was to ascertain the robustness of the ZMAC-1 cell line and its susceptibility to infection by PRRS virus. In addition, we sought to determine optimal conditions for the growth of attenuated PRRS virus in the ZMAC-1 cells and to demonstrate that stocks of MLV vaccine prepared in this cell line could be used for commercial purposes.

Characterization of the porcine alveolar macrophage cell line ZMAC-1. The ZMAC-1 macrophage line has exhibited a very robust growth pattern with a doubling time of approximately 72 hours (FIG. B1; this corresponds to FIG. 4A). We have been able to adapt the cells to be grown in 75 $cm^2$ flasks and to keep this type of cell culture in continuous production for the last 15 months. To date, we have generated more than 1 billion cells from an initial starting population of a few thousand. In order to ensure the perpetuity of this valuable cell line more than 100 frozen cells stocks have been prepared. Every lot has at least 10 vials, and each vial contains at least 2-3 million cells. Upon thawing a representative vial of every lot, we have determined that these vials have >90% viable cells which exhibit vigorous growth within 4 days after re-initiation of their culturing. This cell line has been confirmed to be of swine origin by the reactivity of 100% of the cells in the population with the monoclonal antibody K252.1E4, which is specific for porcine CD45 (Schnitzlein and Zuckermann, 1998; Zuckermann et al., 2001). In addition, the ZMAC-1 cells express the following cell surface markers: CD14, CD163, CD172, MHC class II, whose presence is characteristic of macrophages (FIG. 2).

FIG. B1 (corresponds to FIG. 4A). Growth kinetics of the ZMAC-1 cell line. Established cultures of ZMAC-1 cells in 75 $cm^2$ flasks containing 2-3.2×$10^5$ cells/ml medium were combined with an equal volume of fresh medium to achieve a cell density of 1-1.6×$10^5$ cells/ml. Cells were counted at day 0, 3 and 6 days after fresh medium was delivered into the culture flask.

Growth of PRRS virus in ZMAC-1 cells. The ZMAC-1 cell line is 100% susceptible to infection by PRRS virus, as evidenced by the successful immunofluorescence staining for viral proteins at 20 hr after infection (FIG. B2; corresponds to FIG. 5A). Moreover, we have determined that the first round of replication of PRRS virus is completed by 9 hr after infection (data not shown) and that the peak yield of virus progeny is achieved by the second round of replication at 19 hr after infection (FIG. B3; corresponds to FIG. 4B).

FIG. B2 (corresponds to FIG. 5A). Expression of PRRS virus nucleocapsid protein in ZMAC-1 cells. At 20 hr after infection with PRRS virus strain NADC-20 at MOI of 1, the cells were fixed and stained with FITC-labeled, anti-PRRS virus nucleocapsid mAb SDOW17.

FIG. B3 (corresponds to FIG. 4B). Multiple step growth curves of PRRS virus in ZMAC-1 cells. A suspension of ZMAC-1 cells at 1×$10^6$/ml was infected at an MOI of 0.02 with the attenuated PRRS virus isolate Prime Pac. After a one-hr incubation at 37° C. the inoculum was removed by centrifugation and the cells suspended in medium at a concentration of 1×$10^6$/ml. One-tenth ml aliquots were removed at the indicated times after infection and used for determining the presence of infectious virus ($TCID_{50}$ in MARC-145 cells). Objective 2. Determine the immunogencity and efficacy of a PRRS modified live virus vaccine produced in the porcine macrophage cell line ZMAC-1. The goal of this aim was to compare the levels of protective immunity elicited by the same PRRS MLV vaccine, in this case the Prime Pac PRRS virus, produced in either the ZMAC-1 cell line or in MARC-145 cell line.

To test the efficacy of the of the Prime Pac PRRS virus vaccine, that had been prepared in either ZMAC-1 or MARC-145 cells, groups of pigs were either immunized with vaccine virus derived from one of the two cell lines or mock-treated. At the time of challenge, 4 weeks after immunization, the average body weight (BW) of all 18 pigs in the study was 117±8.6 lb. Since no significant differences between the average BW of vaccinated and non-vaccinated animals was observed, vaccination with the MLV propagated in either ZMAC-1 or MARC-145 cells had no obvious impact on animal growth. In contrast, at 7 days after challenge with the virulent NADC-20 isolate, the unvaccinated pigs had an average BW loss of −5±4 lb while the unchallenged animals gained on average 19.7±6 lb (FIG. 6). An average BW gain of 8.2±5.2 and 9.3±3.6 lb, that were not statistically different from each other, were also noted for the groups that had previously received the MLV virus vaccine prepared in either ZMAC-1 or MARC-145 cells, respectively. Thus, regardless of the type of cell used to propagate the virus, the Prime Pac MLV vaccine was equally effective at diminishing the negative effect of the exposure to virulent PRRS virus on growth, as evidenced by the significant BW loss of PRRS virus-naïve pigs that had been exposed to a heterologous virulent virus 7 days earlier. Remarkably, analyses of the virus load in serum and lung lavage samples from PRRS virus-immunized and challenged animals revealed that the vaccine virus grown in ZMAC-1 cells was significantly (P=0.015) more effective at reducing the extent of viremia at 7 days post-challenge (FIG. 7) and also at eliminating virulent virus from their lungs by 10 days post-challenge (FIG. 8).

FIG. 6. Weight change in pigs after exposure to wild-type PRRS virus. The body weights of PRRS virus-naïve (n=3) and immunized (n=6 for each type of cell-generated vaccine) animals were measured immediately prior to and at 7 days after challenge with the wild-type PRRS virus isolate NADC-20. Measurements were also made at these time points for the unchallenged, PRRS virus-naïve animals (n=3). Changes in weight during the 7-day interval were averaged for members of each group and these values±the standard error are shown. An asterisk (*) Indicates that the group mean is statistically different (P<0.01) from the challenged, PRRS virus-naïve control animals. Two asterisks (**) are used to indicate that the group mean is statistically different (P<0.01) from the unchallenged, PRRS virus-naïve control animals.

FIG. 7. Extent and frequency of viremia in pigs after exposure to wild-type PRRS virus. Serum samples were collected from PRRS virus-naïve and immunized animals immediately prior to and at the indicated days after challenge with the wild-type PRRS virus isolate NADC-20. Samplings were also taken at these time points for the unchallenged, PRRS virus-naïve animals. The level of virus load in the serum was determined by performing titration in MARC-145 cells and then averaged. The data represents the average level of viremia for each group. The ratio next to the symbols indicates the number of viremic pigs (numerator) and the total number of pigs per group (denominator).

FIG. 8. Virus load in the bronchalveolar lavage of pigs after exposure to wild-type PRRS virus. Bronchoalveolar lavage was collected from the lungs of PRRS virus-naïve and previously immunized pigs at 10 days after challenge with the wild-type PRRS virus isolate NADC-20. Samples were also obtained at this time from unchallenged, PRRS virus-naïve animals. The level of virus load in the BAL of each animal was determined by performing titration in MARC-145 cells.

Discussion

The observation that the cell line used to grow the same PRRS MLV vaccine strain can improve the level of protective immunity elicited by this product against a genetically divergent virulent PRRS virus has important implications for developing a highly effective vaccine against this pathogen. Namely, the results of this study suggest that the effectiveness of a PRRS MLV virus vaccine is not, as it is commonly believed, only determined by its genetic similarity to the challenge virus, but is also influenced by how it is produced. A reasonable interpretation for the observations described above is that the biological properties of the vaccine virus were modified in a positive way by simply being grown in ZMAC-1 cells. Consequently, a more effective protective immune response developed in the vaccinated animals. Thus, the results of this study demonstrate that a more effective MLV vaccine against PRRS virus can be created.

REFERENCES FOR EXAMPLE 5

Harms, P. A., Sorden, S. D., Halbur, P. G., Bolin, S. R., Lager, K. M., Morozov, I., Paul, P. S. 2001. Experimental reproduction of severe disease in CD/CD pigs concurrently infected with type 2 porcine circovirus and porcine reproductive and respiratory syndrome virus. Vet Pathol. 38:528-39.

Hill, H., M. JA, K. J J, H. A, and R. C. 2004. PRRS Control: To Hell and Back. American Assoc Swine Veterinarians, Des Moines, Iowa, USA, Mar. 6-9, 2004:369-376.

Mengeling, W. L., K. M. Lager, and A. C. Vorwald. 1999. Safety and efficacy of vaccination of pregnant gilts against porcine reproductive and respiratory syndrome. Am J Vet Res 60:796-801.

Mengeling, W. L., A. C. Vorwald, K. M. Lager, and S. L. Brockmeier. 1996. Comparison among strains of porcine reproductive and respiratory syndrome virus for their ability to cause reproductive failure. Am J Vet Res 57:834-9.

Osorio, F. A., F. Zuckermann, R. Wills, W. Meier, S. Christian, J. Galeota, and A. Doster. 1998. PRRSV: comparison of commercial vaccines in their ability to induce protection against current PRRSV strains of high virulence. Allen D. Leman Swine Conference 25:176-182.

Kwon, B., Ansari, I. H., Osorio, F. A, Pattnaik, A. K. 2006. Infectious clone-derived viruses from virulent and vaccine strains of porcine reproductive and respiratory syndrome virus mimic biological properties of their parental viruses in a pregnant sow model. Vaccine. 24:7071-80.

Schnitzlein, W. M., Zuckermann, F. A. 1998. Determination of the specificity of CD45 and CD45R monoclonal antibodies through the use of transfected hamster cells producing individual porcine CD45 isoforms. Vet Immunol Immunopathol. 60:389-401.

Zuckermann, F. A., Schnitzlein, W. M., Thacker, E., Sinkora, J., Haverson, K. 2001. Characterization of monoclonal antibodies assigned to the CD45 subgroup of the Third International Swine CD Workshop. Vet Immunol Immunopathol. 80:165-74.

Zuckermann, F. A, Alvarez Garcia, E., Diaz Luque, I., Christopher-Hennings, J., Doster, A., Brito, M., Osorio, F. 2007. Assessment of the efficacy of commercial porcine reproductive and respiratory syndrome virus (PRRSV) vaccines based on measurement of serologic response, frequency of gamma-IFN-producing cells and virological parameters of protection upon challenge. Vet Microbiol. 123:69-85.

EXAMPLE 6

Cell Materials and Growth of Cells

Cell materials. Cells designated as ZMAC-1 were prepared and deposited with a recognized International Depositary Authority, the American Type Culture Collection (ATCC; 10801 University Boulevard, Manassas, Va., United States of America) under the Budapest Treaty. The accession number is ATCC Patent Deposit No. PTA-8764 for cells characterized as being of Sus scrofa (pig/swine) lung tissue origin. According to the ATCC Certificate of Deposit document dated Dec. 7, 2007 (Budapest Treaty On The International Recognition Of The Deposit Of Microorganisms For The Purposes Of Patent Procedure; International Form; Receipt In The Case Of An Original Deposit Issued Pursuant To Rule 7.3 And Viability Statement Issued Pursuant To Rule 10.2), the Date of Receipt of Culture is Nov. 14, 2007 for ATCC® Patent Deposit Designation PTA-8764.

Growth of cells. In embodiments of the invention, cells such as ZMAC-1 cells are cultivated in vitro. In general, principles of mammalian cell culture are applied. For example, cells can be cultured in the presence of antibiotics; gentamicin is used but not necessarily required.

Cells are prepared as follows (culture medium: RPMI-1640 supplemented with 10% fetal bovine serum, sodium pyruvate (1 mM; Mediatech Cellgro, Cat. No. 25-000-C1), non-essential amino acids (1×; Mediatech Cellgro Cat. No. 25-025-C1), and Gentamicin (50 mcg/ml; Gibco, Cat. No. 15750-060). The cells are maintained at cell concentrations of about 1 to $5 \times 10e5$ per ml. These cells generally grow in suspension. Discrete colonies of loosely adherent cells can develop but most of the cells will be growing in suspension. Normal cultures will produce floating cell clumps. To reduce adherence, the preferred type of culture flask is Sarstedt Tissue Culture Flask for suspension cell with PE vented cap (Cat. No. 83.1813.502). Established flasks can be harvested every 4-5 days with removal of ⅔ of the fluid and addition of fresh culture medium. New flasks are established by adding at least 3-6 million cells in a 20 ml volume in a T25 flask (minimum of $1.5 \times 10e5$ cells/ml). Growth can be enhanced by adding 2-10 ng/ml of macrophage colony-stimulating factor (mouse; Sigma-Aldrich Product No. M9170). Cell freezing can be accomplished by mixing equal volumes of ice-cold suspensions of cells at 4-8 million cells per ml and ice-cold freezing medium (90% serum, 10% DMSO). Chilled cryovials are filled with the cells suspended in freezing medium and maintained at ice-cold temperature during the process.

Figure 9:
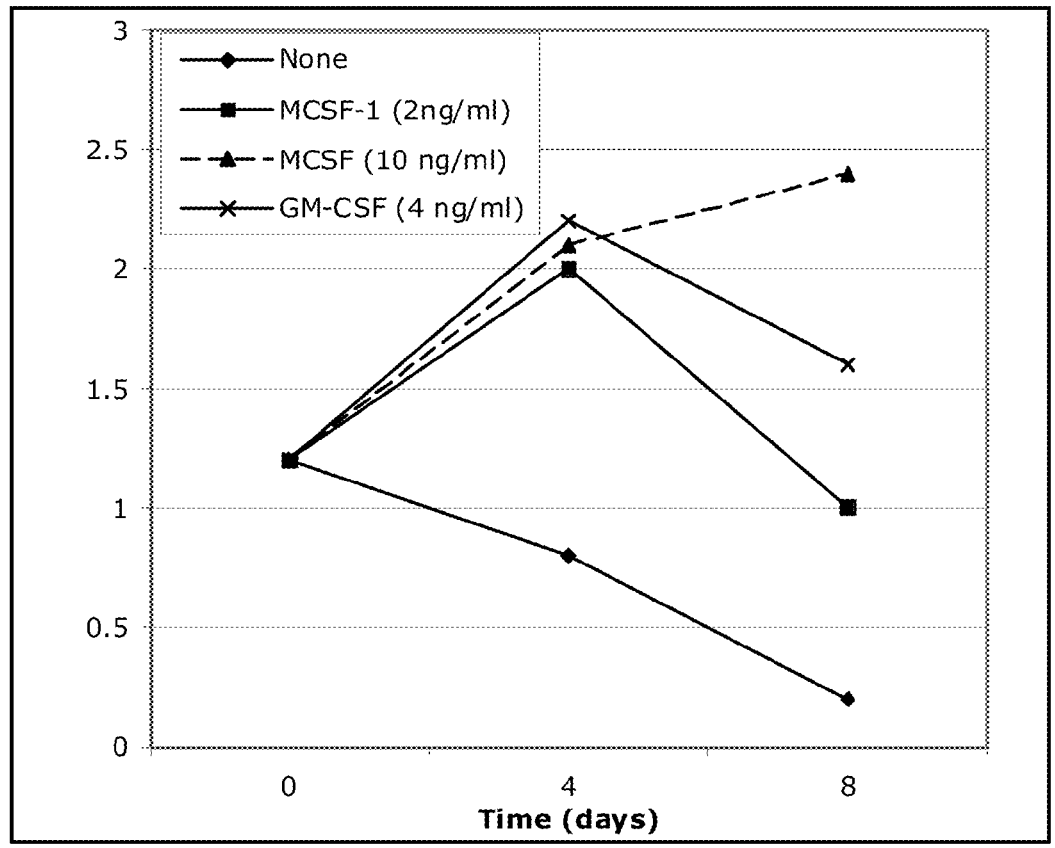
FIG. 9 illustrates growth of ZMAC-1 cells in the presence of growth factors.

FIG. 9 illustrates growth of ZMAC-1 cells in the presence of growth factors. ZMAC-1 cells at $1.2 \times 10^5$ cell per ml, were cultured for 8 days without exogenous growth factor or in the presence of the indicated concentration of either macrophage colony stimulating factor (MCSF) or granulocyte-macrophage colony stimulating factor (GMCSF). The cell concentration was determined with the aid of a hemocytometer at the fourth and eighth day of culture. The y-axis indicates cells/ml ($\times 10^5$).

In an embodiment, a cell of the invention is represented by a cell designated as ZMAC-1 or a deposit with the American Type Culture Collection designated as ATCC Patent Deposit No. PTA-8764 or derived therefrom.

EXAMPLE 7

Generation of Cell Materials and Methods of Isolation from Fetal Porcine Samples Further compositions and methods were developed. In an independent attempt, materials were derived from a sow at 60 days of gestation from the swine herd at the University of Illinois Veterinary Medicine Research Farm (identified as Sow number 5850). Following euthanasia, the uterus was aseptically removed from the abdominal cavity and transported to the cell culture laboratory. Manipulations were generally performed using a bio-safety cabinet under sterile conditions. Six fetuses were aseptically harvested from the uterus and placed in plastic Petri dishes. Lung organs, with the trachea intact and attached to the lung, was dissected away from the heart, esophagus and other membranes. The outside of the lung was thoroughly rinsed with sterile Hank's balanced salt solution (HBSS) to remove any visible blood and other contaminating remaining tissue. Cells in the airways of the lungs from each of the 6 fetuses were isolated separately by bronchoalveolar lavage by placing the lung in a clean and sterile Petri dish and filling the airways with 10 ml of sterile HBSS. The 10 ml of HBSS was propelled into the lung with the aid of a 10 cc syringe and a 1 inch 18 g needle, which was inserted through the lumen of the trachea. The fluid was gently propelled through the trachea while constraining it via compression with forceps to prevent backflow of the HBSS, resulting in the lungs becoming visibly inflated with the fluid. Afterwards the fluid containing the lung lavage cells was self-expelled from the lung by simply releasing the tracheal compression. The cell suspension collected in the Petri dish was transferred to a sterile 15 ml conical plastic tube, and was underlayed with 3-4 ml of warm Ficoll-Hypaque 1077. Immediately afterwards cell suspension was purified via isopycnic centrifugation (400 g for 30 minutes at room temperature).

In an embodiment, cells can be purified by isopycnic centrifugation using Ficoll-Hypaque 1077 either the day of isolation or at a later time, e.g., 1, 2, or 3 weeks later. It is recognized that this purification procedure can facilitate removal of certain components such as red cells, and potentially other material, present in an original preparation. The band of cells obtained after centrifugation at the interface between the Ficoll-Hypaque 1077 and medium was harvested and washed with HBSS twice and the cells recovered each time by centrifugation. After the second centrifugation, the recovered cell pellet from each fetal lung lavage was suspended in culture medium: RPMI-1640 supplemented with 10% fetal bovine serum, sodium pyruvate (1 mM; Mediatech Cellgro, Cat. No. 25-000-C1), non-essential amino acids (1×; Mediatech Cellgro Cat. No. 25-025-C1), and placed independently in one well of 6-well plate (Sarstedt) for suspension culture. Each well was labeled from 1-6 to identify the cells purified independently from each of the six fetuses. Although in this attempt very few and very small cells (<100) were recovered after the isopycnic centrifugation procedure, within 14 days after establishment of the initial cultures, significant growth was observed in every well. Since the macrophage progenitors harvested from the fetal lung were apparently very small and could have a density greater than 1.077 (thus going through the density medium to the bottom of the tube during the isopycnic centrifugation), in the case of fetus #1, the red cell pellet obtained after the isopycnic centrifugation was also harvested and placed in culture and labeled P1. In this case, although the predominant cell type at the initiation of the culture consisted of red blood cells, a small number of very small mononuclear cells was observed. At 16 and 24 days after the initiation of the culture the growth in cells derived from the lung lavage of fetus #4 exhibited sufficient growth to merit splitting into new wells of a 6 well plate. Cells derived from this culture were named ZMAC1107-4. Similarly, growth in the well labeled as P1, which was derived from the red blood cell pellet was clearly evident at 36 days after the initiation of the culture and was also split into 2 wells. Cells derived from this culture were named ZMAC1107-P1. The growth of cells was evident by the presence of cell clusters comprised of 2, 4, 8, 16 or more cells per cluster.

At 37 days after the initiation of the culture of the ZMAC1107-4, the culture medium for this cell line was supplemented in one of duplicate wells with 10 ng/ml of macrophage colony stimulating factor (mouse; Sigma-Aldrich Product No. M9170). Seven days later it was clear that the growth of the ZMAC1107-4 cells had been significantly aided at this early stage of culture by the exogenous supplementation with the growth factor, and thereafter the medium of all cultures was supplemented with MCSF at 5-10 ng/ml. Cultures are fed every 4-6 days by removing by aspiration half the volume of the cell culture and replacing it with fresh medium supplemented with the growth factor. The robust growth of both the ZMAC 1107-4 and ZMAC 1107-P1 lines was evident by the formation of cell colonies growing in suspension and loosely attached to the culture surface.

In another independent attempt, further compositions and methods were developed. A sow identified as number 9093, at 54 days of gestation was obtained from the swine herd at the University of Illinois Veterinary Medicine Research Farm. Following euthanasia, the uterus was aseptically removed from the abdominal cavity and transported to the cell culture laboratory. All manipulations from this point forward were done inside of a bio-safety cabinet under sterile conditions. Eight fetuses were aseptically harvested from the uterus and placed in plastic Petri dishes and their lungs, with the trachea intact and attached to the lung, dissected away from the heart, esophagus and other membranes. The outside of the lung was thoroughly rinsed with HBSS to remove any visible blood and other contaminating remaining tissue. Cells in the airways of the lungs from each of the eight fetuses were isolated separately by bronchoalveolar lavage by placing the lung in a clean and sterile Petri dish and filling the airways with 10 ml of sterile Hank's balanced salt solution (HBSS). The 10 ml of HBSS was propelled into the lung with the aid of a 10 cc syringe and a 1 inch 18 g needle, which was inserted through the lumen of the trachea. The fluid was gently propelled through the trachea while compressing it with forceps to prevent backflow of the HBSS, resulting in the lungs becoming visibly inflated with the fluid. Afterwards the fluid containing the lung lavage cells was self-expelled from the lung by simply reducing compression of the trachea. In some cases the lung was gently pressed down with the blunt end of scissors to help expel the remaining lavage fluid. The cell suspension collected in the Petri dish was transferred to a sterile 15 ml conical plastic tube, and centrifuged for 10 minutes at 1,500 RPM in a table top clinical centrifuge. The recovered cell pellet from each fetal lung lavage was suspended in culture medium: RPMI-1640 supplemented with 10% fetal bovine serum, sodium pyruvate (1 mM; Mediatech Cellgro, Cat. No. 25-000-C1), non-essential amino acids (1×; Mediatech Cellgro Cat. No. 25-025-C1) and placed independently in one well of 6-well plate (Sarstedt) for suspension culture. Each well was labeled from 1-8 to identify the cells purified independently from each of the eight fetuses. Approximately 10,000 cells were initially place in culture from each fetal lung lavage. Growth in these cultures was evident by 5 days. Large clumps of cells were evident in cultures derived from fetuses #1, 3, 6, 7 and 8.

At 12 days after the initiation of the culture the non-adherent and loosely adherent cells from all 8 fetal lung lavage cell cultures were harvested by gently pipetting and purified by isopycnic centrifugation using Ficoll-Hypaque 1077. This was accomplished by transferring the cell suspension to a sterile 15 ml conical plastic tube, which was underlay with 3-4 ml of warm Ficoll-Hypaque 1077 and then centrifuged at 400 g for 30 minutes at room temperature. A clearly visible band of cells was obtained after centrifugation at the interface between the Ficoll-Hypaque 1077. Medium was harvested and washed with HBSS twice, and the cells were recovered each time by centrifugation. After the second centrifugation, the recovered cell pellet from each individual fetal lung lavage culture was suspended in 3 ml of culture medium: RPMI-1640 supplemented with 10% fetal bovine serum, sodium pyruvate (1 mM; Mediatech Cellgro, Cat. No. 25-000-C1), non-essential amino acids (1×; Mediatech Cellgro Cat. No. 25-025-C1), and placed independently in one well of 6-well plates (Sarstedt) for suspension culture and labeled 1-8, which corresponded directly to the original labeling of the cultures. Five days later all cell cultures were fed 2 cc of fresh culture medium. Nine days later significant growth of cells in suspension as well as adherent cells was evident in cultures derived from fetal lung lavage cell cultures labeled 3 and 6, which exhibited a significant number of macrophage colonies growing in suspension as well as loosely adherent round macrophages. A number of large spherical syncytial cells, surrounded by small macrophages forming a structure appearing as a cellular crown, were observed. At 26 days after the beginning of the culture, the cell cultures were fed fresh medium supplemented with 5 ng/ml of MCSF (mouse; Sigma-Aldrich Product No. M9170). Five days later vigorous growth of cell macrophage colonies growing in suspension as well as loosely adherent on the surface of the culture plate was observed in cultures derived from fetuses #3, #6 and #8. These lines were named ZMAC1207-3, ZMAC1207-6, and ZMAC1207-8 respectively and were expanded a few days later by transferring to T75 flasks in culture medium supplemented with 5-10 ng/ml of MCSF.

STATEMENTS REGARDING INCORPORATION BY REFERENCE AND VARIATIONS

All references mentioned throughout this application, for example patent documents including issued or granted patents or equivalents; patent application publications; unpublished patent applications; and non-patent literature documents or other source material; are hereby incorporated by reference herein in their entireties, as though individually incorporated by reference. In the event of any inconsistency between cited references and the disclosure of the present application, the disclosure herein takes precedence. Some references provided herein are incorporated by reference to provide information, e.g., details concerning sources of starting materials, additional starting materials, additional reagents, additional methods of synthesis, additional methods of analysis, additional biological materials, additional cells, and additional uses of the invention.

All patents and publications mentioned herein are indicative of the levels of skill of those skilled in the art to which the invention pertains. References cited herein can indicate the state of the art as of their publication or filing date, and it is intended that this information can be employed herein, if needed, to exclude specific embodiments that are in the prior art. For example, when composition of matter are claimed herein, it should be understood that compounds known and available in the art prior to Applicant's invention, including compounds for which an enabling disclosure is provided in the references cited herein, are not intended to be included in the composition of matter claims herein.

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Thus as used herein, comprising is synonymous with including, containing, having, or characterized by, and is inclusive or open-ended. As used herein, "consisting of" excludes any element, step, or ingredient, etc. not specified in the claim description. As used herein, "consisting essentially of" does not exclude materials or steps that do not materially affect the basic and novel characteristics of the claim (e.g., relating to the active ingredient). In each instance herein any of the terms "comprising", "consisting essentially of" and "consisting of" may be replaced with either of the other two terms, thereby disclosing separate embodiments and/or scopes which are not necessarily coextensive. The invention illustratively described herein suitably may be practiced in the absence of any element or elements or limitation or limitations not specifically disclosed herein.

Whenever a range is disclosed herein, e.g., a temperature range, time range, composition or concentration range, or other value range, etc., all intermediate ranges and subranges as well as all individual values included in the ranges given are intended to be included in the disclosure. This invention is not to be limited by the embodiments disclosed, including any shown in the drawings or exemplified in the specification, which are given by way of example or illustration and not of limitation. It will be understood that any subranges or individual values in a range or subrange that are included in the description herein can be excluded from the claims herein.

The invention has been described with reference to various specific and/or preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be employed in the practice of the invention as broadly disclosed herein without resort to undue experimentation; this can extend, for example, to starting materials, biological materials, reagents, synthetic methods, purification methods, analytical methods, assay methods, and biological methods other than those specifically exemplified. All art-known functional equivalents of the foregoing (e.g., compositions, methods, devices, device elements, materials, procedures and techniques, etc.) described herein are intended to be encompassed by this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, preferred embodiments, and optional features, modification and variation of the concepts herein disclosed may be resorted to by those skilled in the art, and that such modifications and variations are considered to be within the scope of this invention as defined by the appended claims.

REFERENCES

U.S. patents: U.S. Pat. No. 5,510,258 issued Apr. 23, 1996 by Sanderson et al.; U.S. Pat. No. 5,587,164 issued Dec. 24, 1996 by Sanderson et al.; U.S. Pat. No. 5,476,778 by Chladek et al., issued Dec. 19, 1995; U.S. Pat. Nos. 6,241,990; 6,110,468; 6,042,830 issued 2000 Mar. 28; U.S. Pat. No. 5,989,563 issued 1999 Nov. 23; U.S. Pat. Nos. 5,846,805; 6,660,513; 7,081,342; 6,806,086; 6,500,662; 6,498,008; 6,455,245; 6,251,404; 6,197,310; 5,583,053; 6,210,963; 5,840,563; 5,925,359 issued Jul. 20, 1999; U.S. Pat. No. 5,698,203 issued Dec. 16, 1997.

United States Patent Application Publication No. 20060063151; US20030219460A1 by David et al. (Cotton rat lung cells for virus culture; cell line ATCC PTA-3930); US 20050271685 by Calvert et al.

PCT International Publication No. WO9835023A1 published Aug. 13, 1998; WO9855626A2 published Dec. 10, 1998

EP0610250B1; US6033844

Delputte P L et al. Porcine arterivirus infection of alveolar macrophages is mediated by sialic acid on the virus. Journal of Virology (2004), 78(15), 8094-8101

Wissink et al. Identification of porcine alveolar macrophage glycoproteins involved in infection of porcine respiratory and reproductive syndrome virus. Archives of Virology (2003), 148(1), 177-187

Weingartl H M, et al. Continuous porcine cell lines developed from alveolar macrophages. Partial characterization and virus susceptibility. Journal of Virological Methods (2002), 104(2), 203-216

Delputte P L et al. Involvement of the matrix protein in attachment of porcine reproductive and respiratory syndrome virus to a heparinlike receptor on porcine alveolar macrophages. Journal of Virology (2002), 76(9), 4312-4320

CHIOU, Ming-T et al., Effects of porcine reproductive and respiratory syndrome virus (isolate tw91) on porcine alveolar macrophages in vitro. Veterinary microbiology (2000), 71(1-2), 9-25

Opriessnig T et al., J of Virology, December 2002, p. 11837-11844. Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV.

Naviaux R K et al., Journal of Virology, August 1996, 70(8):p. 5701-5705.

Kim D, et al., Cell Biol Int. 2005 August; 29(8):638-46.

Counter C M, et al., 1998 Oncogene 16:1217-1222.

Zuckermann F A, Zsak L, Mettenleiter T C, Ben-Porat T. Pseudorabies virus glycoprotein gIII is a major target antigen for murine and swine virus-specific cytotoxic T lymphocytes. J. Virol. 1990 February; 64(2):802-12.

Lowe J E et al., 2005; J Am Vet Med Assoc 226:1707-11.

Meier W et al., 2000, Vet Res. 31:41.

Meier W A et al., 2003, Virol. 309:18-31.

Meier W A et al., 2004, Vet. Immunol. Immunopathol. 102:299-314.

Mengeling W L et al., 1999, Am J Vet Res 60:796-801.

Mengeling W L et al., 1996, Am J Vet Res 57:834-9.

Osorio F A, 1998, Allen D. Leman Swine Conference 25:176-182.

Sanchez-Torres C et al., 2003, Arch Virol. 148:2307-23.

Sanchez C et al., 1999, J Immunol 162:5230-7.

Neumann E J et al., 2005, J Am Vet Med. Assoc. August 1; 227(3):385-92

Vincent A L et al., Viral Immunol. 2005; 18(3):506-12.

Bautista E M et al., J Vet Diagn Invest. 1993 April; 5(2):163-5.

Kwon B et al., Vaccine. 2006 Nov. 30; 24(49-50):7071-80. Epub 2006 Jul. 21.

Zhang R, Yang H, Li M, Yao Q, Chen C. Acceleration of endothelial-like cell differentiation from CD14+ monocytes in vitro. Exp Hematol 2005 33:1554-63

Schmeisser A, Garlichs C D, Zhang H, Eskafi S, Graffy C, Ludwig J, Strasser R H, Daniel W G. Monocytes coexpress endothelial and macrophagocytic lineage markers and form cord-like structures in Matrigel under angiogenic conditions. Cardiovasc Res. 2001 Feb. 16; 49(3):671-80.

Mayani and Lansdorp, Blood. 1994 May 1; 83(9):2410-7.

Bridell et al, Blood. 1992 Jun. 15; 79(12):3159-67.

I claim:

1. A method of isolating a cell from a porcine fetal lung, comprising the steps of providing a porcine fetal subject; obtaining a cell-containing sample from said subject; separating a cell from said sample, and culturing the sell for at least 5 passages, wherein the cell is capable of replicating porcine reproductive and respiratory syndrome (PRRS) virus; thereby isolating said cell.

2. A method of isolating a cell from a porcine fetal lung, comprising the steps of providing a porcine fetal subject; obtaining a cell-containing sample from said subject, wherein said cell-containing sample is a bronchoalveolar lavage sample; and separating a cell from said sample, wherein the cell is capable of replicating PRRS virus; thereby isolating said cell.

3. The method of claim 1, wherein the separating step is by density gradient centrifugation.

4. The method of claim 1 wherein the cell is a macrophage.

5. The method of claim 1, further comprising growing the cell for at least 10 days in continuous culture.

6. The method of claim 1, wherein the culturing is for at least 10, 20, or 50 passages.

7. The method of claim 1, wherein the porcine fetal subject is from about 30 to about 90 days of gestational age.

8. A method of isolating a cell from a porcine fetal lung, comprising the step of providing a porcine fetal subject; obtaining a cell-containing sample from said subject, separating a cell from said sample, and subcloning the cell, wherein the cell is capable of replicating PRRS virus; thereby isolating said cell.

9. The method of claim 1, further comprising culturing the cell in a growth medium comprising a growth factor composition.

10. The method of claim 9, wherein the growth factor composition comprises macrophage colony stimulating factor (MCSF) or granulocyte-macrophage colony stimulating factor (GMCSF).

11. The method of claim 9, wherein the growth factor composition comprises MCSF at a concentration of 5 to 10 ng/mL.

12. The method of claim 2, wherein the cell is a macrophage.

13. The method of claim 2, further comprising the step of culturing the cell for at least 5 passages.

14. The method of claim 2, wherein the porcine fetal subject is from about 30 to about 90 days of gestational age.

15. The method of claim 2, further comprising culturing the cell in a growth medium comprising a growth factor composition of MCSF or GMCSF.

16. The method of claim 8, wherein the cell is a macrophage.

17. The method of claim 8, further comprising the step of culturing the cell for at least 5 passages.

18. The method of claim 8, wherein the porcine fetal subject is from about 30 to about 90 days of gestational age.

19. The method of claim 8, further comprising culturing the cell in a growth medium comprising a growth factor composition of MCSF or GMCSF.

20. The method of claim 4, wherein the macrophage is an alveolar macrophage.

* * * * *